United States Patent
Allan et al.

(10) Patent No.: US 6,703,005 B2
(45) Date of Patent: *Mar. 9, 2004

(54) PROCESS FOR THE PRODUCTION OF A DEODORANT OR ANTIPERSPIRANT PRODUCT

(75) Inventors: Peter Stewart Allan, Uxbridge (GB); Michael Andrew Browne, Wirral (GB); Elfriede Maria Langeveld, Wirral (GB); Paul Lloyd, Wirral (GB); Reginald Manley, Wirral (GB); Paul Reissen Rennie, Wirral (GB); Frederick Edmund Stocker, Wirral (GB); Karnik Tarverdi, Uxbridge (GB); Jacqueline Marie Thorpe, Wirral (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 247 days.

This patent is subject to a terminal disclaimer.

(21) Appl. No.: 09/827,385

(22) Filed: Apr. 5, 2001

(65) Prior Publication Data

US 2001/0041169 A1 Nov. 15, 2001

(30) Foreign Application Priority Data

Apr. 5, 2000 (GB) .............................................. 0008392

(51) Int. Cl.[7] .......................... A61K 7/32; A61L 9/012; A61C 9/01; B29C 47/10; B29C 47/60
(52) U.S. Cl. .............................. 424/65; 424/65; 424/66; 424/401; 424/DIG. 5; 514/944; 514/951; 264/102; 264/211.21; 264/212; 264/211.23; 141/82; 222/251
(58) Field of Search ........................... 424/65, 66, 401, 424/DIG. 5; 514/944, 951; 264/102, 211.21, 212, 211.23; 141/82; 222/251

(56) References Cited

U.S. PATENT DOCUMENTS

| 4,678,420 A | 7/1987 | Inoue | 425/144 |
| 4,688,609 A | 8/1987 | Diaz | 141/82 |

(List continued on next page.)

FOREIGN PATENT DOCUMENTS

| EP | 556 957 | 8/1993 |
| EP | 135 315 | 4/1995 |

(List continued on next page.)

OTHER PUBLICATIONS

Database USPATFULL on STN, US 5525597 (Hainrihar et al.), abstract, Jun. 1996.*
Database CAPLUS on STN, WO 9108670–A1 (Guerrini), abstract, Jun. 1991.*

(List continued on next page.)

Primary Examiner—Frederick Krass
Assistant Examiner—Clinton Ostrup
(74) Attorney, Agent, or Firm—Kevin J. Stein

(57) ABSTRACT

A deodorant or antiperspirant soft solid composition is filled into dispensing containers by injection moulding, i.e. under pressure, preferably in the vicinity of its normal setting temperature. The deodorant or antiperspirant composition is preferably continuously produced in a screw extruder, especially a twin screw extruder, controlled to deliver the composition in a suitably viscous state under low shear and particularly for formulations in which a particulate antiperspirant is suspended in a fluid carrier. The pressure in the injection head at the point of injection is greater than 120 kPa and in many instances from 800 to 2000 kPa. The combined process offers benefits for controlled fill of dispensing containers, particularly for formulations incorporating sensitive ingredients and offers tolerance in composition temperature at the time of fill.

32 Claims, 2 Drawing Sheets

U.S. PATENT DOCUMENTS

| | | | | |
|---|---|---|---|---|
| 4,837,399 A | * | 6/1989 | Baker et al. | 514/468 |
| 4,876,395 A | * | 10/1989 | Kissinger | |
| 4,983,637 A | * | 1/1991 | Herman | 514/724 |
| 5,008,470 A | | 4/1991 | Powell | |
| 5,091,591 A | * | 2/1992 | Cipullo | |
| 5,135,741 A | | 8/1992 | Park | 424/66 |
| 5,260,342 A | * | 11/1993 | Herman | 514/724 |
| 5,270,344 A | * | 12/1993 | Herman | 514/725 |
| 5,316,712 A | | 5/1994 | Ono et al. | 264/102 |
| 5,324,867 A | * | 6/1994 | Asaoka | |
| 5,350,836 A | | 9/1994 | Kopchick et al. | |
| 5,490,979 A | * | 2/1996 | Kasat et al. | 424/66 |
| 5,498,709 A | * | 3/1996 | Navia et al. | 536/124 |
| 5,525,597 A | * | 6/1996 | Hainrihar et al. | 514/75 |
| 5,681,570 A | * | 10/1997 | Yang et al. | 424/197.11 |
| 5,780,426 A | * | 7/1998 | Palladino et al. | 514/9 |
| 5,874,155 A | * | 2/1999 | Gehrke et al. | 428/134 |
| 5,885,559 A | | 3/1999 | Lee et al. | 424/65 |
| 6,284,951 B1 | * | 9/2001 | Eby | 800/312 |
| 6,338,840 B1 | * | 1/2002 | Allan et al. | 264/102 |

FOREIGN PATENT DOCUMENTS

| | | | | |
|---|---|---|---|---|
| FR | 2 194 113 | | 2/1974 | |
| GB | 2169601 A | * | 7/1986 | C07H/5/02 |
| JP | 2000-327614 | * | 11/2000 | |
| WO | WO 9108670 A1 | * | 6/1991 | A01N/65/00 |
| WO | 97/12680 | * | 4/1997 | B01L/3/14 |
| WO | 00/19861 | | 4/2000 | |

OTHER PUBLICATIONS

The Condensed Chemical Dictionary, 10$^{th}$ Ed., Gessner G. Hawley, Van Nostrand Reinholg Co., New York (1981), pp. 252, 602 and 603.*

Merriam–Webster's Collegiate Dictionary, 10$^{th}$ Ed., Merriam–Webster, Inc., Springfield, MA (1998) p. 355.*

Rajendar S. Varma and Rajendar Dahiya Tetrahedron, 1998, vol. 54, pp 6293–6298.*

Paoletti, Lawrence C. et al The Journal of Biological Chemistry, 1990, vol. 265, No. 30, pp 18278–18283.*

Skolnick et al., 2000, Trends in Biotech. 18:34–39.*

Bork, P., 2000, Genome Research 10:398–400.*

Doerks et al, 1998, Trends in Genetics 14:248–250.*

Smith et al., 1997, Nature Biotechnology 15:1222–1223.*

Brenner, et al, 1999, Trends in Genetics 15:132–133.*

Bork et al. 1996, Trends in Genetics 12:425–427.*

Pilbeam et al., 1993, Bone 14:717–720; see p. 717.*

Nichols et al., Establishment of germ–line–competent embryotic stem (ES) cells using differentiation inhibiting activity, 1990, Development, vol. 110, p. 1341–1348.*

PCT International Search Report in a PCT application PCT/EP 01/02824.

Derwent Abstract of FR 2 194 113—published on Mar. 29, 1974.

Patent Abstract of Japan 58189112—published Nov. 4, 1983.

* cited by examiner

PROCESS FOR THE PRODUCTION OF A DEODORANT OR ANTIPERSPIRANT PRODUCT

TECHNICAL FIELD

The present invention relates to a process for the production of a deodorant or antiperspirant composition, and particularly to a soft solid composition. The invention further relates to the incorporation of such a composition in a dispensing container, and to a product produced thereby.

BACKGROUND AND PRIOR ART

Deodorant or antiperspirant compositions in soft solid form have achieved a significant market share in many countries in recent years. A soft solid product conventionally comprises the composition in a container, which is usually in the form of a canister or barrel provided at one end with a closure perforated by one or more apertures and at the opposite end with elevator or piston means for urging the canister contents through the aperture in the closure. Such compositions flow readily when subjected to pressure, but when the pressure is released stiffen and cease to flow or flow only very slowly. Accordingly, they remain as on the top surface of the closure and are distributed topically by rubbing the closure across the chosen area of body skin, and particularly in the axilla or other sweaty parts of the body.

Soft solid products are conventionally manufactured by casting premixed compositions into the canister or barrel, those two terms being used interchangeably herein. In conventional hot casting processes, the constituents of a deodorant or antiperspirant soft solid composition are mixed in a large vessel, and heated to form a mobile composition. Whilst the composition is in a mobile and readily pourable state, it is poured into the barrel. The composition is thereafter cooled or permitted to cool until it is non-flowing. A top closure or base is fitted to the barrel, depending on whether bottom fill or the more normal top fill has been employed.

There are several disadvantages associated with preparing a large volume of molten deodorant or antiperspirant. First, in such batch processes, the composition usually remains in a molten state for a long period, not only whilst it is being prepared, but also whilst it is being cast into the barrels. During this period, heat is dissipated, thereby increasing the overall energy consumption for the process. Secondly, the maintenance of a relatively high temperature needed to keep the composition molten for an extended period can cause the degradation of some common constituents, such as the oxidation of waxes or fats, resulting potentially in rancid odours that need to be masked by additional perfume. Moreover, such temperatures also constrain the incorporation of heat sensitive constituents, such as the perfume or malodour masking fragrances, on account of the likelihood that the composition smell will be different for the last barrels filled compared with those filled at the beginning of the batch. It is important to maintain a fragrance which is reasonably constant within a batch.

Moreover, in addition to processing and filling times of individual batches, there is potentially a significant holding time for fractions of master batches which are prepared for example to produce variants.

In addition, the conventional batch process is poorly suited to switching between different formulations in view of the time taken to cleanse the apparatus between batch preparations to avoid cross contamination.

Various soft solid formulations can be obtained by subjecting firm structured formulations to an appropriate level of shear during the preparative and/or filling stages of the manufacture process, thereby rupturing a certain extent the structure. However, tight control of the shearing process is needed so as to avoid excessive shearing or shearing under inappropriate conditions which can result in an excessively runny material or undue separation of the composition constituents during storage, thereby retaining enough structure to inhibit the material from flowing easily under its own weight when present in its container or when deposited on the skin, but producing a product which is capable of flowing though dispensing apertures when subjected to mild pressure. An excessively runny material has the attributes of a lotion rather than a soft solid and would require a different type of dispenser, and undue constituent separation can manifest itself in syneresis problems, ie presence of a liquid phase which can readily leak from the barrel during storage or in use.

A further difficulty can arise because the composition must be kept mobile whilst it is being fed from its production/storage vessel to the filling station so as to avoid line blockage which would be extremely disruptive to production. In practice, this means that during the casting operation, the composition is usually introduced into the barrel at a temperature that is still significantly above its set temperature. As a consequence of a high fill temperature, the composition is likely to remain for a relatively long period of time within the barrel in a mobile state during which segregation can arise, particularly in respect of particulates, such as active antiperspirant materials, intended to be distributed reasonably evenly throughout the composition. Segregation is inherently undesirable for users of the product, because its performance can vary depending on how much of the product has been consumed.

In EP 135315 to the Mennen Company, there is described a process in which a batch of a soft solid antiperspirant composition is subject to shear mixing until the formulations has cooled below its normal setting temperature. Shear mixing in the vicinity of the normal setting temperature is designed to impair structure formation, in order to allow the composition to retain a lower viscosity and flow more freely. However, batches take a considerable period to be filled into the containers. This means that the composition cast into the last containers has been subjected to shear mixing for a much longer period of time than the material which was cast first. Accordingly the Theological properties of the product can alter between the first and last products cast.

For some soft solid products, there is a related manufacturing process, but one which is carried out at a temperature that is at or relatively close to ambient temperature, depending on local conditions and, often, in the region of about 25 to 35° C. This is sometimes called a cold fill process. In such a process, the formulation is subjected to shear mixing throughout and is cast with difficulty into containers, because its viscosity is relatively high and approaching that which it will eventually attain after storage in the container. Close control of the processing is required to minimise the risk of pipe blockage and incomplete filling of the containers.

Therefore, there is a need for a process that is capable of producing soft solid products containing deodorant or antiperspirant compositions which overcomes or ameliorates one or more of the problems identified hereinbefore or disadvantages associated with the existing casting process.

Apparatus and methods for injecting thermoplastics into moulds are known and used. For example, in U.S. Pat. No. 4,678,420 to Inoue, assigned to Inoue (Japax Research Inc), there is described apparatus in which a thermoplastic is fed through a hopper into a single screw mixer, plasticised and injected into a mould. Such apparatus and methods do not provide teaching that is directly applicable to producing products comprising soft solid deodorant or antiperspirant composition in a dispensing container, due to very different structuring mechanisms and the different constraints on processing thermoplastics into moulds compared with soft solid antiperspirant or deodorant formulations into dispensing containers.

In U.S. Pat. No. 4,688,609 (Diaz) assigned to Fluid Packaging Company, there is described a system for producing firm sticks of a deodorant composition in which a large vat of molten deodorant composition is produced, and progressively delivered into stick barrels through dispensing apparatus injected at an operating pressure of 10–15 psi and within which the composition is maintained in a molten state by hot water jackets. The disclosure provides no teaching as to how to ameliorate or overcome the disadvantages of a batch manufacture process nor does it indicate how to employ an injection process for filling soft solids into a dispensing container.

In U.S. Pat. No. 5,316,712 to Ono et al assigned to J. O. Cosmetics Co Ltd, there is described a process for producing solid cosmetics in which a cosmetic base containing a powder and oil is fed into a single screw which rotates within a heated chamber to mix and heat the constituents. The screw reciprocates within the chamber to inject the cosmetic base into a mould. The process is applied to producing cosmetics such as lipstick eye-shadow or foundation having an extremely high content of particulate materials such as talc or mica under high shear and very high pressure conditions without cooling to the vicinity of the set temperature of the cosmetic base. Such a combination of conditions is not applicable to the satisfactory injection moulding of deodorant or antiperspirant soft solid compositions, because the high shear would tend to destroy the composition structure to such an extent that a lotion would be created and remain so when the composition attained ambient, and the very high injection pressures would risk ejecting a significant fraction of the soft solid out of the dispensing container.

The present inventors have found that some of the problems associated with the prior art processing of deodorant or antiperspirant compositions can be ameliorated or overcome by employing a continuous method for producing or dispensing a mobile feed of the deodorant or antiperspirant composition for supply to apparatus for dispensing the composition into soft solid containers.

The present inventors have also found that some or other problems associated with prior art processing of deodorant or antiperspirant compositions to produce soft solids can be ameliorated or overcome by injecting a mobile deodorant or antiperspirant composition into a dispensing container at an elevated pressure, and at a temperature controlled such that the composition is partially structured at the moment when it is injected into the dispensing container.

Furthermore, it is desirable to identify and employ a method for producing a mobile soft solid composition that is suitable for feeding to an injection unit, and preferably one which can ameliorate overcome or circumvent one or more of disadvantages inherent in a conventional batch process for producing mobile soft solid compositions.

SUMMARY OF THE INVENTION

By employing a continuous method for producing a mobile feed, it is possible to reduce significantly the inventory of molten material, to reduce energy consumption during processing, to minimise oxidation of constituents and to minimise any deleterious effects on heat-sensitive constituents.

Alternatively or additionally, by injecting a mobile deodorant or antiperspirant composition into a dispensing container at an elevated pressure, the manufacturer is enabled to employ composition which is partially structured at the moment of fill. By so doing, good quality product in accurately controlled amounts can be obtained avoiding or ameliorating problems of blockage, and/or inhomogeneity, syneresis and segregation of ingredients. In addition, production benefits such as shorter cooling times for the product are also achievable, and/or the reduction of cooling capacity for the products, possibly even as far as the total absence of forced cooling capacity, and/or the shortening the length of residence time on the line after filling and before packing.

According to one aspect of the present invention, there is provided a process for forming a deodorant or antiperspirant soft solid product comprising heating a deodorant or antiperspirant composition where necessary to form a mobile composition and delivering the mobile composition into a filling station for filling a dispensing container characterised in that the mobile composition is injected into the dispensing container under a pressure of above 120 kPa in the injection head for at least a fraction of the time in which the composition is being introduced into the dispensing container.

A soft solid formulation herein commonly has a measured hardness will of from 0.003 to 0.5 Newton/mm$^2$, and Frequently from 0.003 up to 0.1 Newton/mm$^2$. Hardness can conveniently be measured using a Stable Micro-systems TA.XT2i Texture Analyser, equipped with a metal sphere of 9.5 mm diameter, its 5 kg load cell, an impact speed of 0.05 mm/s to a depth of 7 mm and the data analysed using Texture Expert Exceeds™ software. Firm solids have a hardness of greater than 0.5 Newton/mm$^2$ and particularly from 0.75 Newton/mm$^2$.

By injecting the mobile soft solid composition under pressure into a dispensing container, it is possible to accurately fill containers, thereby minimising the risk that containers will be underfilled, whilst avoiding excessive overfill of a significant proportion of containers. Moreover, such a process enables a soft solid to be filled into containers despite variation in its viscosity, and also convenient filling when its viscosity has increased below that which is suitable for a cast filling process. Accordingly, this is of considerable benefit not only for hot filling processes, by enabling a lower fill temperature, but also for cold filling processes by reducing risks of premature blockage and inconsistent filling of containers.

In a related aspect of the present invention, there is provided a process for forming deodorant or antiperspirant soft solid products comprising heating a deodorant or antiperspirant composition where necessary to form a mobile composition and delivering the mobile composition to a filling station for filling a dispensing container characterised in that the mobile composition is at least partially structured at the moment that it is injected into the dispensing container.

In the present invention, deodorant or antiperspirant compositions are considered to be at least partially structured if they have developed structure that is detectable by physical techniques, for example when a pattern is generated in X ray diffraction or when the composition has a temperature in the vicinity of its normal setting temperature. Other means for introducing structure can comprise fibrous networks. Additionally or alternatively, deodorant or antiperspirant compositions can be considered to be at least partially structured if they contain a gellant/structuring agent and the temperature of the composition is below its nucleation temperature. The presence of at least partial structure can be deduced when the viscosity of the formulation is detectably higher than its minimum achievable by increasing its temperature or subjecting it to excessive shear.

Thus, the present invention comprises an apparatus for forming deodorant or antiperspirant soft solid products comprising a means for applying injection pressure to a deodorant or antiperspirant composition to inject the composition into a dispensing container and a substantially separate means adapted for feeding the deodorant or antiperspirant composition to the means for applying injection pressure.

The means for feeding deodorant or antiperspirant composition to the means for applying injection pressure can conveniently comprise the apparatus for continuously producing mobile material, directly or via a buffer chamber, such as the process summarised or described hereinafter.

Desirably, a process for producing a mobile soft solid formulation that is suitable for feeding to an injection unit comprises introducing the constituents of said soft solid formulation into a twin screw extruder within which said constituents are mixed and transported to an outlet. This process can be carried out continuously, and the outlet can be connected directly or via a buffer to the injection unit. The screw extruder preferably has two parallel screws with intermeshing flights.

By controlling the rate of production of the mobile composition to match the rate at which the composition is dispensed into the containers, the producer is, in effect, producing the mobile material on demand from its constituents at the rate set by the filling equipment. Consequently, the inventory of material held at an elevated temperature, such as molten material, is controlled at or near its minimum. This also has the effect of minimising the period whilst the material is kept at an elevated temperature before it is dispensed into its containers, thereby reducing heating costs and the period during which constituents can oxidise or degrade, eg heat sensitive constituents. It has the further effect of enabling the manufacturer to avoid using a large holding and/or mixing tank for batch processing. Such tanks need to be cleaned out between production batches, and especially when the formulation changes. This is not only a time consuming exercise, but it is also wasteful of the volume of material adhering to the sides of the tank. The use of a continuous process according to this aspect of the invention is especially beneficial in that it is flexible because changes can be made with only minimal loss of inventory during a changeover. Accordingly, it can respond rapidly to small or large changes in the formulation, such as fragrance variations, or formulation variations intended to tailor the immediate product to local markets. Moreover, an in-line compounding process, as contemplated herein, can avoid preparing and holding a part formed master batch.

Although the screw extruder can be employed to transport, mix and heat to a desired tempertaure a preformed composition, it is particularly desirable to employ the screw extruder as an in-line compounder to produce a mobile deodorant or antiperspirant composition continuously at a rate matched with the rate at which the composition is introduced into the dispensing containers.

A screw extruder represents a practical and beneficial means to transport a mobile deodorant or antiperspirant composition at a controllable rate to a filling station that enables the composition to be mixed effectively or kept mixed during transportation, using appropriately designed mixing elements and optionally also offers an opportunity for controlling the timing of introduction of constituents such as heat or oxidation sensitive constituents into a mobile composition, possibly shortly before the composition reaches the filling station. Furthermore, by controlling the screw speed of the screw extruder, the elements contained therein and the temperature of the formulation as it is conveyed along the extruder, it is possible to control the rate of shear of the formulation and thereby affect the extent of structuring of the formulation and in consequence its viscosity.

The concept of producing the fluid deodorant or antiperspirant composition continuously can, if desired, be combined with the concept of continuously transporting the fluid composition using a screw extruder towards a filling station, either sequentially linked, or by a screw extruder with appropriate infeed means for some or all of the constituents of the composition and means for heating and temperature control of the composition during its transportation along the screw.

The filling of mobile material into dispensing containers or moulds in a single line is punctuated by alternate periods when material is not being filled, particularly whilst a filled dispensing container is being removed from the filling station and replaced by an empty dispensing container. In order to accommodate continuous production of mobile material and its intermittent dispensing, it is highly desirable to interpose a buffer chamber between the means for continuously producing or transporting the mobile composition and the means for filling it into containers or moulds, the buffer chamber being dimensioned to hold at least the volume of composition produced whilst filling is not taking place.

The deodorant or antiperspirant composition can be introduced into the means for feeding in any suitable state, such as, for example, fluid, semi-solid or particulate form. They can be introduced separately or pre-mixed, if desired. It has been discovered that a screw extruder provides a particularly effective means of continuously feeding a soft solid deodorant or antiperspirant composition, including particularly compositions supplied in a mobile state, to a filling station, which can comprise especially an injection moulding means. The screw feeder can comprise a screw extruder suitable or adapted for in-line compounding.

In batch processing of formulations containing a particulate antiperspirant, one further problem has been identified, namely the formation of grit. Carlson et al in U.S. Pat. No. 5,417,964 has described the formation of grit from agglomeration of antiperspirant active particles, in which the particles are suspended in a carrier vehicle which is solidified with high and low-melting components, particularly waxes. Carlson also discloses that grit formation detracts from the aesthetics of the product. This in fact applies not only to solids but similarly to soft solids. Carlson discloses the results of considerable investigation and experimentation in which water of hydration in the antiperspirant salt is driven off, condenses on the mixing vessel walls and cover, corrodes the walls and cover, becoming contaminated with metals, falls back into the formulation in the vessel and acts to attract and agglomerate the antiperspirant particles. The resultant agglomerates are not only aesthetically displeasing to the touch, but are also unattractive visually, being dark specks in a pale or white-coloured formulation.

The instant inventors have recognised that it is undesirable to produce a formulation that is gritty. This is applicable especially when the formulation is intended to be injected into a dispenser, because the injection nozzle that they contemplate using potentially has a narrow outlet, but is also applicable in subsequent cast filling processes too.

Accordingly, in a further aspect of the present invention there is a provided a process for producing a mobile soft solid formulation that is suitable for feeding to an injection unit which comprises the steps of introducing the constituents of said soft solid formulation into a twin screw extruder, mixing said constituents at an elevated temperature thereby forming a mobile mixture and transporting the mixture to an outlet from the screw extruder wherein the formulation comprises a carrier fluid in which is suspended a particulate antiperspirant material.

Such a process advantageously avoids or ameliorates the problem of grit formation. The constituents can be introduced individually or some or all pre-compounded together. Without being bound by any theory, the inventors believe that the use of a screw extruder for mixing and transporting a suspended particulate antiperspirant formulation reduces the average residence time of material during processing is considerably shorter than in a batch process, which accordingly reduces the extent of the cycle of water being driven off from the antiperspirant, condensing and being returned to the formulation. Moreover, the apparatus is believed to avoid or minimise relatively cold contact surfaces adjacent to hot formulation and thus the inventors postulate that the risk of any evaporated water condensing is minimised.

Although the screw extruder is especially suited to producing a soft solid in which a particulate antiperspirant is suspended in a fluid carrier, such as hydrophobic oils, thickened or structured such that the product has a hardness of below 0.5 Newtons/mm$^2$, the inventors recognise that similar advantages accrue in respect of products in which the hydrophobic oil is structured to produce a firm stick.

In a further aspect of the present invention, there is provided a soft solid deodorant or antiperspirant product obtainable by any process according to the present invention and particularly a product obtainable using an injection moulding process.

It has been found that the process described herein for transporting the formulation to the injection moulding apparatus or in-line compounding the formulation is well suited for incorporating additive or benefit agents such as those which are immiscible with other constituents in the deodorant or antiperspirant composition and/or which can degrade or interact destructively with some other constituent when subjected to heat and particularly heat for a prolonged period. Accordingly, the present invention provides deodorant or antiperspirant soft solid products obtainable by the process of the present invention comprising a deodorant or antiperspirant composition containing one or more constituents which are readily oxidised and/or are sensitive to prolonged heat. Alternatively, they could be immiscible with other constituents of such compositions.

In a still further aspect, the present invention provides for a method for incorporating a sensitive or oxidisable constituent into a deodorant or antiperspirant composition, comprising adding the sensitive or oxidisable constituent to a deodorant or antiperspirant composition which is at least partially structured or adding it immediately prior to being cooled to a temperature at which it becomes partially structured and applying a pressure to the deodorant or antiperspirant composition containing the sensitive or oxidisable constituent so as to inject it into a dispensing container.

In a preferred embodiment, the sensitive or oxidisable constituent is miscible with the deodorant or antiperspirant composition or one phase thereof.

References herein to the invention or to any preferred features apply to all aspects of the invention, unless expressly referring to solely a specified aspect or aspects.

DETAILED DESCRIPTION OF THE INVENTION

By "deodorant or antiperspirant soft solid product" is meant a dispensing container containing a coherent mass containing one or more deodorant and/or antiperspirant active constituents which does not flow under its own weight, but which can be caused to flow through an orifice when subjected to hand pressure. The normal setting temperature of the composition is that at which it ceases to flow in the absence of externally applied pressure. In many instances, this is not sharply defined, and often can vary slightly, depending on how quickly the composition is being cooled.

The deodorant or antiperspirant compositions can comprise homogeneous mixtures, such as solutions, or material suspended or dispersed in a continuous phase. Some particularly desirable compositions comprise one or more particulate antiperspirant active materials suspended in a continuous phase provided by some or all of other constituents.

Except in the Examples or where expressly exempted, numbers given herein, such as limits of ranges, are approximate.

Mobile Composition Production

Continuous production of an antiperspirant or deodorant compositions in mobile form can be effected very conveniently employing a screw extruder equipped with a plurality of infeed ports for solid and liquids spaced axially along the screw, which enable the constituents to be introduced into the screw extruder in an order which takes into account their individual characteristics. Particularly, it is desirable to employ screw extruders which have a series of segments each of which have heating or cooling elements, thereby enabling the user to establish a temperature profile for the composition and its constituents as it is introduced into and conveyed through to the extruder outlet.

The relative order of introduction of the constituents into the extruder is at the discretion of the user, who will normally take into account their known properties, so as to optimise processing. It is preferable for the carrier and structurant to be in fed in the first or early segments. By introducing both at an early stage, it is possible to produce a fluid mass into which other constituents such as particulate antiperspirant or deodorant actives can be introduced.

It is highly desirable to introduce sensitive additives for example readily oxidisable or heat-sensitive additives or agents, such as perfumes, in a segment at or close to the outlet from the extruder, thereby enabling such an additive or agent to be introduced towards the end of the processing, thereby reducing and preferably minimising the length of time that the additive is exposed to elevated temperatures. It will be understood that sensitive additives can also include materials which interact deleteriously with each other or other constituents of the composition whilst it is fluid, especially molten and that reference hereinafter to oxidisable or heat sensitive additives reads on to such other sensitive additives.

It will be recognised that such a choice of point of addition for such oxidisable/heat sensitive additive is likewise applicable where the screw extruder is used for partial in-line compounding, the remaining constituents being premixed and delivered to the inlet end of the conveyer in either solid or molten form.

The temperature profile of the screw extruder is often selected in conjunction with whether a hot or cold filling process is suitable for the soft solid formulation. For hot filling processes, the temperature profile of the screw extruder advantageously employs a high temperature at or near the point of introduction of structurant and carrier, preferably enabling them to form a molten mass, and most suitably in subsequent segments the temperature is controlled progressively lower. This further can reduce degradation of heat sensitive agents that are preferably introduced in segments where a lower temperature is maintained. The temperature of the composition on exiting from the screw conveyer can be controlled to at or slightly above the temperature in the final segment, the difference often being no more than about 3 or 4 degrees C.

Materials which it is believed can interact with other constituents of the formulations and in particular suspended antiperspirant formulations include di or polyhydric materials, such as glycerol. Insufficient di or polyhydric material is present to dissolve the antiperspirant, so that the antiperspirant remains suspended in the carrier fluid, but preferably sufficient is present to impart moisturising properties to the formulation. When it is desired to incorporate glycerol or like materials, it can be advantageous to introduce them subsequent to introduction of the antiperspirant and preferably at a temperature which is no higher than that obtaining in the antiperspirant formulation. This can limit the residence time of interactive materials in the formulation, and particularly limit their presence towards temperatures at which interaction can be relatively low.

Residence time of the formulation, such as sensitive constituents thereof, can be further limited by employing a comparatively high screw speed in the extruder. In practice, though, the screw speed and the formulation temperature are conveniently selected in a combination that is neither too fast at the prevailing temperature nor too low a temperature at the prevailing screw speed such that the mixing process does not impart excessive shear to the subsisting formulation, and thereby the combination prevents structure break-down.

Accordingly, therefore, the twin screw extruder is particularly suitable for producing formulations containing the suspension of the antiperspirant active in a carrier and a polyhydric material present in an amount insufficient to dissolve all the antiperspirant. This is to be distinguished from gelled solution formulations in which the antiperspirant active is dissolved in the polyhydric material.

For a cold-filling process, limited heating of the composition may be desirable to bring its temperature slightly above ambient, such as from 25 to 30° C.

Where the composition is intended to be filled employing a casting technique, as is possible in a class of process according to the first aspect of the present invention, the technique commonly employed commercially, the screw extruder preferably includes a suitable final segment or segments to bring the composition to a suitable temperature for casting, for example if the composition has previously been cooled to enable heat sensitive additives to be incorporated at a lower temperature. This may comprise a final segment to reheat it to its melting temperature. When a cast technique is employed, the formulation is normally maintained at a temperature of several degrees above the normal setting temperature of the formulation, such as from 5 to 10° C. above for hot filling processes or in the region of 25 to 30° C. for cold filling processes. Employment of a smaller temperature difference increases the risk of line blockage between the screw extruder and the cast nozzle, for example to or from a holder tank typically deployed above the filling station to permit the fluid formulation to flow under gravity into the barrel or other container.

Where the filling station comprises injection moulding apparatus, which is preferred and itself comprises several aspects of the present invention, the final segment or segments often provide cooling in order to bring the composition temperature to close to its normal setting temperature, and particularly to within the temperature range (such as those indicated hereinafter) at which it is most beneficial to inject into the dispensing container.

The infeed rates of the constituents of the composition, the dimensions of the screw and its rotation rate and the rate at which the fluid composition is dispensed are all advantageously adjusted to produce matched production and dispensing. Likewise, other screw characteristics, such as pitch of the screw flight are chosen in accordance with the viscosity of the composition, for example to control the pressure in the extruder, eg to enable gas to be vented if necessary or to ease addition of constituents and regulate transportation of the composition. It is highly desirable for the screw extruder to comprise a plurality of parallel screws, each screw being single flighted and intermeshed, and in many instances co-rotational, in order to transport the mobile composition most suitably to the outlet. Two such parallel screws are most convenient in order to provide a forward pumping action. This is especially applicable for soft solid antiperspirant or deodorant composition, and especially material having a viscosity of 10000 cP (milliPas) cP (milliPas) (milliPas) to 1000000 cP (milliPas). The screw or screws are preferably fitted with discs or other means, for example at or near the outlet to provide back pressure.

Use of the temperature controlled screw extruder enables antiperspirant or deodorant compositions to be produced continuously with minimum inventory, especially at elevated temperature and minimum delay before they are dispensed. This very short processing time is especially beneficial for constituents that are sensitive to elevated temperatures or air oxidation. The low inventory is beneficial to reduce composition losses during product variation or if a production mistake occurs.

For the transport and mixing of antiperspirant or deodorant compositions, a screw extruder can be employed that is similar in operation to that employed as an in-line compounder, as described above, but it does not need many of the ports for in-feeding the constituents separately.

It is desirable to employ a twin screw extruder to transport, and where appropriate compound in line, formulations having a viscosity of at least about 10000 cP (milliPas), up to 5000000 cP (milliPas), often up to 1000000 cP (milliPas) and particularly desirable for formulations in the lower fraction of the viscosity range, such as up to 200000 cP (milliPas).

Injection Moulding

Deodorant or antiperspirant soft solid compositions to be introduced into the dispensing container can be in any form capable of being delivered into the container. For example, the composition can be in a substantially fluid form (e.g. molten, molten dispersion, liquid), or substantially semi-solid (ie in the close vicinity of its normal set temperature), so long as the composition is sufficiently mobile to allow the pressure applying means to deliver it into a dispensing container as would be understood by the person skilled in the art.

Structure

The presence of at least partial structure in the deodorant or antiperspirant composition is advantageous and can be ascertained by comparing it with a deodorant or antiperspirant composition which is similar to and at the same temperature as the deodorant or antiperspirant composition under consideration, except for having no structure and/or structuring agent present, or of substantially the same composition at a temperature above its nucleation temperature whereby it can be determined by for example X Ray Diffraction or other techniques whether structure is observable. Alternatively or additionally, structure can be determined by measuring the viscosity of the composition showing that it is detectably higher than in the molten mass.

Structure can be provided, for example, by liquid crystal formation, or by incorporating a polymeric structuring agent or thickeners such as polyamides or polysiloxane elastomers or carboxylated polysaccharides like polycarboxylated dextrin or inorganic thickener or gellant like finely divided silica or a clay or an organic gellant which is not polymeric such as selected dibenzoyl alditols (eg dibenzoyl sorbitol) or selected n-acyl amino derivatives (eg N-acyl glutamide derivatives) or selected hydroxyfatty acids (eg 12-hydroxystearic acid) or selected sterols (eg cholesterol) or selected secondary amides of di or tri basic carboxylic acids, (eg 2-dodecyl-N,N'-dibutylsuccinimide), or a waxy material such as fatty alcohols (eg stearyl alcohol) or a wax or by incorporating a sufficient volume of a dispersed solid component within a continuous liquid phase such that it will increase the viscosity. Gellants often provide structure in the carrier by forming a network, such as a fibrous network, within the composition. A solid component can provide structure by interacting to form a network within the deodorant or antiperspirant composition or through the simple physical interaction/contact of the solid particles with one another or with one or more components of the continuous phase.

Structured deodorant or antiperspirant compositions are usually obtained by introducing one or more structurants for example, waxes, gellants or elastomers (eg crosslinked partially crosslinked or non-crosslinked organopolysiloxanes), or inorganic thickeners such as clay, silica and/or silicate material (including in situ formed aluminosilicates) and a contribution to composition thickening can be provided by particulate antiperspirants such as aluminium and/or zirconium salts. The invention in-line compounding and injection moulding processes described herein are particularly suitable for formulations that employ one or more wax structurants.

Structurants are normally incorporated in the deodorant or antiperspirant composition at concentrations sufficient to impart coherence to the material when it is not being subjected to pressure, and the actual concentration depends on the chemical nature of the structurant. In many instances, the structurant, other than an active antiperspirant compound, is selected in the range of from 0.1 to 30% by weight and the antiperspirant is often selected in the range of from 1 to 40% by weight of the deodorant or antiperspirant composition. Further composition preferences are described hereinafter.

The existence of internal structure in the deodorant or antiperspirant composition may be due to the components used, their concentration, the temperature of the composition and the shear to which the composition is being or has been exposed.

The presence of such internal structuring, ordering or anisotropy may be typically revealed by the temperature/viscosity/shear profile of the composition in a manner known to the person skilled in the art. In some instances, the presence of structure gives rise to non-Newtonian fluid behaviour.

The presence and identity of a crystal structuring system in a deodorant or antiperspirant composition may be determined by means known to those skilled in the art. In addition to or substitution for X-ray diffraction, for example, optical techniques, various rheometrical measurements, neutron diffraction, and sometimes, electron microscopy can be employed. As will be known to the person skilled in the art, structure may be detected by the use of polarised light microscopy. Isotropic phases have no effect upon polarised light, but anisotropically structured phases will have an effect upon polarised light and may be birefringent. An isotropic liquid would not be expected to show any kind of periodicity in X-ray or neutron diffraction micrographs, whereas structure may give rise to first, second or even third order periodicity, in a manner which will be known to the person skilled in the art.

Preferably, the deodorant or antiperspirant composition is in a semi-solid state when delivered to the dispensing container. A deodorant or antiperspirant composition may be considered to be in a semi-solid state if sufficient structure is present in the composition so that it no longer behaves like a simple liquid, as would be understood by the person skilled in the art.

In some instances, we have found that it is possible to obtain deodorant or antiperspirant compositions in the form of a soft solid having good physical properties by cooling a deodorant or antiperspirant composition into a partially structured phase prior to its delivery into the dispensing container.

The injection moulding processes and apparatus of the present invention therefore provide a means for producing good quality deodorant or antiperspirant soft solids products from deodorant or antiperspirant compositions which do not necessarily lend themselves readily to the known casting methods of manufacture, for example, formulations which would show significant sedimentation, and in particular, employing injection temperatures in the vicinity of the normal setting temperature of the composition. By so doing, it is possible to improve the distribution of particulates through the soft solids, particularly the vertical distribution. Such a technique for producing an improved, i.e. more even, particle distribution in a soft stick enables the user to contemplate employing a particulate active having a larger average particle size than when employing an otherwise identical composition in a conventional casting process.

The deodorant or antiperspirant compositions of the present invention can typically be more viscous than those employed in prior art cast processes or other processes in which the composition is dispensed in a more molten, less viscous state, usually at considerably above its normal setting temperature. Consequently, the invention process employing injection of the composition into the dispensing container employs a higher pressure than that contemplated in the prior art gravity fed processes.

By the use of a pressurised injection filling technique, and particularly injection filling in conjunction with controlled low shear mixing, for example in a screw extruder and especially in a twin screw extruder, it is possible to obtain a soft solid product having a higher viscosity that that of similar products produced conventially by cast filling. This widens the window for preparing soft solids by enabling a wider range of formulations to be produced as soft solids.

Where the processing technique itself increases the viscosity of the product compared with the viscosity obtained by conventional processing techniques, at least part of the benefit can be taken by reducing the proportion of structurant employed. This releases volume in the formulation for incorporating additional benefit agents or can enable a more cost effective product to be produced by incorporating additional carrier.

Injection Pressure

The pressure applied to the deodorant or antiperspirant composition in contact with the pressure applying means is referred to herein as the "applied pressure", and references to "apply" and "applying" pressure to a deodorant or antiperspirant composition refer to the applied pressure. on account of the viscosity of the deodorant or antiperspirant composition, the pressure experienced by the composition further down the flow path may be lower.

"Injection pressure" is the pressure on the deodorant or antiperspirant composition exerted in the injection head at the point in time that the composition enters the dispensing container.

It has been found that injection pressures can be used which are sufficiently high to deliver a deodorant or antiperspirant composition which is below its normal setting temperature into a dispensing container without compromising the final structure of the antiperspirant or deodorant product. As contemplated in the second aspect of the invention, use of injection pressures in excess of 120 kPa, and particularly in excess of 200 kPa can allow soft solids compositions to be fed successfully into a dispensing container that are either difficult or not possible to cast. The injection pressure in the head is in many instances selected in the range of at above 500 kPa. The injection pressure is normally not higher than 5000 kPa, and for many conditions is no higher than 3000 kPa, particularly no higher than 2500 kPa. In a particularly suitable range, the injection pressure is at least 800 kPa and often not more than 2000 kPa. An injection pressure selected within the foregoing ranges, taking into account the physical characteristics of the composition and the other prevailing physical parameters, offers practical benefits in injecting the antiperspirant or deodorant compositions, and particularly when the composition is being injected near or below its normal setting temperature.

Applied pressures, often in the order of up to 6000 kPa, may be used to deliver deodorant or antiperspirant compositions into the dispensing container, the pressure usually being selected in accordance with the viscosity of the compositions. Excessive shear should be avoided during the introduction of the composition into the dispensing container so as to avoid possibly irreversible breakdown of the structure, and at injection pressures contemplated herein, excessive shear can be avoided by controlling process parameters such as temperature, flow rate and apparatus design. The injection pressure is often calculated taking into account the rheology of the composition being injected. The injection pressure in the head is preferably controlled at below 3000 kPa. This is not only in order to lower the risk of structure impairment, but also to reduce or eliminate the risk of material being injected into the mould or especially into a barrel, at such a velocity that it bounces out to a significant extent.

Injection under the controlled injection pressures indicated above is desirably employed in conjunction with a selected injection temperature, such as in the vicinity of the normal setting temperature of the composition. Conveniently, this can indicate between 5° C. above or below and in many instances up to about 3° C. above the normal setting temperature.

Composition Temperature

It has been found that deodorant or antiperspirant compositions can be delivered into a dispensing container at lower temperatures than those typically employed in casting operations, by subjecting them to pressure, without compromising the final structure of the deodorant or antiperspirant product, by selecting appropriate injection conditions including as a significant factor, the temperature of the composition relative to its normal setting temperature. Most deodorant or antiperspirant compositions for injection according to the instant invention have a regular melting temperature, which is usually not above 120° C. and which is usually significantly higher than its regular set temperature. Injection is often conducted at a temperature of at least 10° C. below its regular melting temperature. In practice, the temperature range within which a composition is injectable depends on the chemical constitution of that composition and the selection of the actual injection temperature takes that into account. Where the presence of structure in a deodorant or antiperspirant composition to be delivered to the mould can be clearly identified, and the deodorant or antiperspirant composition remains mobile without the application of excessive shear, the composition can be injection moulded. Excessive shear can be avoided at such temperatures by controlling process parameters such as flow rate and apparatus design.

A practical deodorant or antiperspirant composition in soft solid form will be in an apparently solid state, i.e. set, at ambient and usually remain set at normal storage and/or use temperatures, which are normally in the range of 10 up to 20–30° C., but flow under applied pressure.

Accordingly, the deodorant or antiperspirant composition preferably enters the dispensing container at a temperature above ambient, and in the hot filling process, especially at above 30° C., and in many instances above 40° C.

The temperature of the deodorant or antiperspirant composition on introduction into the dispensing container in an injection moulding process according to the present invention is normally chosen in conjunction with the composition constituents. In many instances, the injection temperature is selected within the range of from 40 to 95° C. In a number of compositions such as those structured with one or more waxes, optionally in conjunction with an organic thickener and/or a fibre-forming organic gellant, it is convenient or desirable to fill at a temperature of from about 40 to 65° C. It can be highly desirable to control the temperature of the composition on introduction into the dispensing container to close to its normal setting temperature, for example within about 5° C. However, an advantageous benefit of using a pressurised injection technique is that by relevant choice of injection pressure, it possible to fill over a wider range of temperatures than for cast filling, such as in the region of 10° C. below its normal setting temperature. Such low fill temperatures are not contemplatable in cast filling. Higher than normal setting temperatures can be contemplated also using a pressurised injection system, thereby retaining the benefit of accurate dosing. The practical temperature range for injection filling a selected formulation usually can be identified by measuring the viscosity/shear/temperature profile and selecting conditions to provide suitable low shear and adequate viscosity, such as to fill accurately an acculumalator interposed the injection head and the pressure means to it.

In many instances in a hot fill process, the composition is often heated to a temperature above its normal melt temperature, possibly as much as 30° C. above and conveniently from 5 to 20° C. above and thoroughly mixed. Heat or oxidation sensitive constituents such as perfume are advantageously introduced into the composition only shortly before it is filled, and the composition is cooled during delivery to the filling station to a temperature in the region of its normal setting temperature.

The use of a pressure injection technique often enable a lower filling temperature for the composition, thereby reducing the likelihood of forced external cooling being required with its concomitant investment in plant and space and running costs, or reducing the time that the product remains at a significantly elevated temperature, thereby reducing holding time before the product can be boxed for storage and transportation.

It is a noteworthy advantage in many aspects of the present invention that the deodorant or antiperspirant composition is able to enter the dispensing container at a lower temperature than in a simple casting technique. Moreover, it is quicker and easier to control the temperature of the composition during its production and delivery compared with inside the dispensing container. For that reason, less energy overall may be required, and also because the operating temperatures can be lower. The present invention therefore offers economy in operation.

In other processes, sometimes called cold fill processes, the injection temperature is in the region of 25 to 35 or 40° C. In such processes, the main structurant is usually not a wax, but instead comprises an inorganic thickening agent.

Injection Moulding Apparatus

Injection moulding is a process which has been previously particularly used in the moulding of articles from synthetic thermoplastic or thermosetting polymers, particularly articles having thin cross sections and complex shapes from thermoplastic polymers.

In essence, an injection moulding apparatus for plastic material comprises a substantially closed mould and a means for delivering the plastic material under raised pressure into the substantially closed mould. High pressures are commonly employed. Preferably, there are means for raising the temperature of the plastic material to a temperature where the material is flowable under pressure. The process of the present invention can be carried out using low shear injection moulding apparatus that is capable of employing materials having a comparatively low viscosity, with or without any means for heating the feed. Preferred modifications according to the present invention are discussed below.

Deodorant or antiperspirant compositions according to the present invention can be injection moulded using an apparatus comprising a means for applying pressure to the deodorant or antiperspirant composition in the injector head so as to inject the composition into a dispensing container. A "means for applying pressure" is defined as a device capable of containing a material and of applying a pressure to that material so as to force it into a dispensing container. The container is typically open to the atmosphere.

Suitable types of apparatus that lend themselves to injecting a deodorant or antiperspirant composition into a dispensing container include positive displacement pump-type arrangements such as, for example, a piston pump. Gear pump and lobe pump-type arrangements can be contemplated.

One suitable apparatus is a simple ram extruder in contact with a receiving container. Such an apparatus typically comprises a reservoir or barrel for the deodorant or antiperspirant composition, a plunger for applying pressure to the material in the reservoir and an exit port through which the deodorant or antiperspirant composition is impelled, directly or indirectly, into a receiving container, advantageously with suitable control to minimise or prevent wallslip. A ram extruder apparatus is particularly applicable for injection moulding of deodorant or antiperspirant compositions. Valve controlled inflow into and/or outflow from the reservoir can ensure accurate dosing and reduce or eliminate composition dripping between injections.

Injection moulding apparatus as described above may be used in the processes of the invention.

In a preferred embodiment, the deodorant or antiperspirant composition is preferably at least partially structured when delivered to the dispensing container. Preferably, the deodorant or antiperspirant composition is in structured form when delivered to the mould, such as within 5° C. of its normal setting temperature.

In order to control the shear to which the deodorant or antiperspirant composition is subjected, the nature of the deodorant or antiperspirant composition itself needs to be taken into account, and in particular its viscosity and structure at various temperatures. To control the shear, it is desirable to control process parameters such as the temperature, pressure applied to the composition, flow rate of deodorant or antiperspirant composition in the apparatus and configuration of the apparatus. Configurations such as severe bends, constrictions and fast moving parts can subject the deodorant or antiperspirant composition to high shear, and accordingly it is advisable to avoid them.

Any suitable method may be used to control the temperature of the composition being injected into the dispensing container. It may be supplied at a temperature suitable for delivery to the dispensing container and require no alteration to its temperature. Alternatively, and preferably, the temperature of the composition is altered before or whilst it is fed to the dispensing container by using heating or normally cooling means to respectively raise or lower the temperature of the composition as is appropriate.

In many embodiments, the state of the deodorant or antiperspirant composition is altered before or whilst it is being fed to the filling apparatus. For example, it may pass from a completely molten state to a more viscous state, eg by cooling the composition bringing it close to or below its normal setting temperature.

Any suitable cooling or heating means may be applied to the injection moulding apparatus in which the deodorant or antiperspirant composition is contained/passes during the injection moulding process.

Suitable heating and cooling means are well-known to the skilled person in the art. For example, a suitable cooling means is a cooling jacket containing a cooling medium, and suitable heating means include, for example, electrical heating jackets containing a heating medium or heat exchangers of various forms.

Advantageously, the temperature profile of the deodorant or antiperspirant composition is controlled such that it is initially sufficiently high to melt and keep molten its organic constituents, and is progressively cooled until immediately prior to the point of injection into the dispensing container, it has a suitable viscosity.

A plurality of separately controllable heating means or cooling means may be provided at different positions in the apparatus. A stepped temperature profile can then be provided in the direction of flow of deodorant or antiperspirant composition. For example, the temperature may increase or decrease in steps.

Deodorant or antiperspirant compositions for soft solid formation in accordance with the present invention are normally produced by mixing their constituents in the desired proportions under conditions providing a molten phase and feeding the resultant fluid mixture to apparatus dispensing measured amounts into containers or moulds. Consequently, a process for producing the soft solid products from the constituents of the compositions encompasses both a means for feeding a fluid mixture as well as the means for applying injection pressure to the deodorant or antiperspirant composition.

Accordingly, the present invention employs an apparatus for forming a deodorant or antiperspirant product comprising a means for applying pressure to a deodorant or antiperspirant composition to deliver the composition to a mould and a substantially separate means adapted to feed the deodorant or antiperspirant composition to the means for applying pressure to the deodorant or antiperspirant composition.

The feeding means can be considered to be substantially separate when no parts of the feeding means have any significant role in applying pressure to the deodorant or antiperspirant composition. In practice, the feeding means is suitably in fluid connection with the means for applying pressure to the deodorant or antiperspirant composition, whereby the deodorant or antiperspirant composition can be readily fed into the means for applying pressure. Examples of suitable feeding means include a ram feeder, and especially a screw extruder, the latter possibly also acting as an in-line compounder, or a combination thereof.

It is especially desirable in the present invention to employ a non-reciprocating screw extruder as the means for transporting the antiperspirant or deodorant composition, optionally with in-line compounding of the composition, to the apparatus which fills the mould or container, such as in particular by injection moulding, and especially to employ an extruder (preferably non-reciprocating) with twin intermeshing flights. Such extruders are particularly suited to the transportation of antiperspirant or deodorant compositions, under conditions controllable to minimise or avoid the risks of breakdown of the structure of the compositions during transportation, whilst enabling good mixing. On the other hand, reciprocating extruders can have an increased tendency to introduce gas (air) into antiperspirant or deodorant formulation during processing, which can impair the finish and homogeneity of the final product.

When the deodorant or antiperspirant composition is provided to the injection moulding apparatus in a substantially mobile form, then a cooling zone can often be employed in the injection apparatus instead of or in addition to a heating zone. If molten composition is created at a temperature of at least 10° C. or more above the normal setting temperature of the soft solid composition, it is preferably cooled prior to being delivered into the dispensing container. Naturally, it will be understood that deodorant or antiperspirant compositions can be introduced into the dispensing container at any appropriate temperature such as those described herein and that furthermore, a heating apparatus could be used to maintain such a temperature, if need be.

It is a preferred feature of the feeding means that it is capable of supplying a continuous feed of deodorant or antiperspirant composition.

The means for feeding deodorant or antiperspirant composition may feed the composition to the means for applying pressure or to a zone preceding the means for applying pressure such as a heating or cooling zone. In a preferred embodiment, the means for feeding deodorant or antiperspirant composition feeds the composition into an accumulator zone which provides an interface between the continuous operation of the feeder and the discontinuous injection cycle of the pressure applying means.

Means for controlling the temperature of the deodorant or antiperspirant composition may be provided at any position in the injection moulding and feeder apparatus. For example, such heating or cooling means may be provided in the means for applying pressure, in the feeding means or in a separate zone, or in any combination thereof. A separate heating zone may be placed, for example, between the means for feeding deodorant or antiperspirant composition and means for applying pressure.

The present invention provides for the use of screw extruders in conjunction with the injection moulding apparatus, either as the feeding means, pressure applying means or both. In suitable apparatus, the means for applying pressure to the prepared (e.g. thermally heated) material is provided by the screw itself. Very preferably a twin co-rotating screw extruder is employed.

The means for applying pressure to the deodorant or antiperspirant composition may comprise the tip of a screw extruder, as described above for known injection moulding apparatus. Alternatively, separate means for delivering a composition under pressure can be used, as set out below.

Preferably, the means for feeding deodorant or antiperspirant composition comprises a feeder in the form of a screw feeder. This is found to give particularly smooth feed.

Screw geometry may be designed to suit the formulation being processed. The rotational speed of the screw or screws is controllable to provide an acceptable flow rate of material to the accumulation zone or means for applying pressure, without applying unacceptable shear to the composition.

There are particular problems with conveying fluid deodorant or antiperspirant composition. Single screw extruders rely on drag flow for conveying, and therefore to convey fluids they need to be specifically designed with a close clearance and/or inclined so that gravity aids the forward flow of material. It is particularly preferred to have two parallel screws with intermeshing, preferably self-wiping flights which provide positive displacement to propel deodorant or antiperspirant composition forwards. The screws may rotate in opposite directions (counter-rotating) but are preferably co-rotating to reduce the reverse pressure flow and shear in the nip region. Such twin-screw extruders with intermeshing flights for delivering liquids or solids are known to the skilled person though not hitherto recognising expressly if they might be employed for mobile antiperspirant or deodorant compositions, nor recognising that such apparatus is capable of transporting and mixing (for in-line compounding) such antiperspirant or deodorant compositions during the generation of at least partial structure within the composition prior to its dispensing in subsequent filling apparatus. Twin-screw extruders are of particular benefit in transporting and mixing (in line compounding) antiperspirant or deodorant compositions having a typically limited content of particulate material, such as not more than 50% by weight, and often from 0 or 20% to 35% by weight particulates.

It is of practical importance to provide a pressure chamber in fluid contact with the feed means, eg a screw extruder as described above, where material can accumulate, comprising at least one wall defined by a piston which is movable to increase or decrease the volume of the pressure chamber, and in fluid contact with at least one injection nozzle.

In a preferred embodiment, the screw extruder, in addition to feeding material for injection moulding into the means for applying pressure, will also perform the function of preconditioning the material to a desired physical state for injection. By providing the screw extruder such as those mentioned hereinbefore (and particularly a twin screw extruder)

with one or more heating and/or cooling zones, and by selecting, for example, appropriate screws, pitches, screw alignment and screw speed, the material fed into the extruder can be intimately mixed and structured to whatever extent is required for the particular injection moulding process being used and product characteristics sought. For example, in a preferred embodiment of the present invention, material to be injected is in a substantially semi-solid state.

In addition, the feeding means, preferably a screw extruder, can contain intermediate ports for degassing and/or for adding further constituents. Additives, such as, for example, dyes and fragrances and materials which are readily oxidisable or are heat sensitive can also be added through appropriately located intermediate ports along the length of the screw feed.

By employing a screw feed with a temperature profile, and especially a temperature profile in which the temperature is high enough to melt meltable solids such as waxes and the temperature is progressively lower towards the outlet from the screw feeder, it is possible to produce the composition from its constituents and introduce additives and/or materials which are readily oxidisable or are heat sensitive to the bulk flow of material in the feeder at a specific temperature, the temperature and location of addition points individually or together often being selected to minimise the likelihood of oxidation or degradation and/or the period in which it can take place.

The screw extruder can constitute a partial or complete in-line compounder. It is convenient when it acts as a partial compounder to use it to introduce the more readily oxidisable or heat sensitive constituents. By so doing it is possible to produce in a continuous manner a fluid deodorant or antiperspirant composition for dispensing, for example using an injection moulder. In addition, the material in the screw feed can be mixed and/or structured to a greater or lesser extent as it moves within the screw feed depending on the equipment and process parameters employed. It is thus possible to add constituents and/or additives and/or materials which are readily oxidisable or are heat sensitive to the bulk flow of material when it is at a chosen level of viscosity and/or mixing and/or structuring.

Accordingly, the screw extruder represents a convenient and readily controlled means for producing deodorant or antiperspirant composition continuously. By appropriately dimensioning the screw extruder and controlling the screw speed, it can produce a fluid composition at a rate that is matched with the rate at which the composition is dispensed, and in a form which is suitable for dispensing in an injection moulder, for example a composition which is at least partially structured.

Injection Nozzle

The means for applying pressure to the deodorant or antiperspirant composition can be connected to the dispensing container by a simple passage, or a passage having non-return means or connections for bypass ducts, to allow quick withdrawal of the pressurizing means after the dispensing container is filled and smooth operation of the apparatus.

In a preferred embodiment, however, the deodorant or antiperspirant composition is fed through a nozzle whose length is a significant proportion (at least half, preferably at least three quarters) of the length of the internal volume of the dispensing container. It has been found that there can be a problem in simple filling with jetting or "snaking" of the material in the dispensing container. By providing a nozzle which extends substantially to the distant end of the dispensing container, good fill has been found to be possible.

Preferably, the nozzle and dispensing container move axially relative to each other whilst the deodorant or antiperspirant composition is being introduced into the dispensing container. The dispensing container may be moved with respect to the injection head and/or the nozzle may be moved with respect to the dispensing container whilst the deodorant or antiperspirant composition is being delivered. The rate at which the nozzle and dispensing container move relative to each other is preferably matched with the rate of delivery of the deodorant or antiperspirant composition, and where the cross section varies, the rate of movement takes into account the change in variation to the cross section of the dispensing container so that the nozzle remains just below the surface of deodorant or antiperspirant composition in the dispensing container. This has been found to give particularly good fill. In a preferred embodiment, the nozzle is moved with respect to the dispensing container.

The nozzle may be heated or pre-heated in order, for example, to prevent any of the deodorant or antiperspirant composition solidifying (depositing) in the nozzle and thus inhibiting smooth delivery of the composition into the dispensing container.

Preferably, the internal diameter of the injection nozzle for use with the means for delivering deodorant or antiperspirant composition under pressure is small, and in practice is principally constrained by the internal diameter of the dispensing container or the aperture into the mould through which the composition is intended to be injected. In many instances, the nozzle internal diameter is in the range 1 to 20 mm, preferably 3 to 10 mm and of circular section. In other instances, the cross sectional shape of the nozzle can correspond to the internal shape of the dispensing container.

A cut-off valve may be located between the composition feeder and the injection nozzle preventing further discharge of composition into the container after a predetermined volume has been injected.

Dispensing Container

The container for deodorant or antiperspirant soft solids often comprises a composition reservoir such as a barrel or pouch, provided at one end with a closure defining one or more apertures through which the soft solid can pass through under pressure for topical application to the skin. The reservoir may be rigid or flexible. A cap for the closure is normally provided, often having inward facing protrusions that engage the apertures in the closure to prevent unwanted egress of the container contents during storage.

In rigid containers, the barrel is often tubular, commonly being round or oval in transverse cross section. The rigid container for soft solids often further comprises a transport mechanism for moving the piston axially along the container. One conventional transport mechanism comprises a helically threaded aperture, usually at the centre of the piston, which engages with a similarly threaded rod which extends axially within the soft stick and which is mounted perpendicularly from and co-axially with a rotatable wheel or a pawl and ratchet mounted at the base of the container. On rotation of the wheel or depression of the pawl, the rod is rotated, the threads of the rod engage with the threads on the aperture in the embedded plate and the piston bearing the soft stick is moved axially. Other transport mechanisms known with in the art can also be employed.

When the container reservoir comprises flexible side walls such as in a pouch made from a flexible sheet material, the sidewall is squeezed, normally manually to deliver the soft solid out of the reservoir.

Rigid containers or those with limited flexibility are often made from a plastics material such as polyethylene or polypropylene. The flexible side wall can comprise a flexible sheet material which is impermeable to the antiperspirant or deodorant composition, and is often made from a sheet of a thermoplastics material such as identified above or a metal foil, or from a laminate of a plastics material and a metal foil.

The thermoplastics materials preferably do not melt until they reach a temperature significantly above the temperature at which the composition enters the container. Many such materials do not melt until they reach a temperature in the region of 100° C. or higher. The rigid containers and closures for both rigid and flexibly walled containers are themselves often produced by injection moulding.

Most conveniently, the container is top filled and the closure subsequently fitted. If the container is filled through the bottom of the barrel, the aperture in the closure is normally reversibly sealed, for example by a removable covering strip.

The dispensing container may be pre-cooled or preheated prior to delivery of composition into it.

After filling with deodorant or antiperspirant composition, the container can be cooled in a cooling zone to encourage rapid solidification of the composition, if desired. However, as referred to hereinbefore, in a number of preferred embodiments, the cooling zone is omitted.

The filling process may be carried out in a quasi-continuous manner by having a plurality of containers passing through a feed station where the deodorant or antiperspirant composition is injected under pressure in to each container in turn and subsequently taken through the steps of cooling, where necessary. As a further option, a plurality of dispensing stations can be fed from a single production or delivery apparatus, such as in particular a screw extruder, for example through a manifold located after the accumulator.

In injection moulding processes according to the present invention, it is generally not necessary to provide a separate means for venting, i.e. removal of air as the container is filled, because the opening in the container though which it is filled is normally significantly greater than the external diameter of the injection nozzle. However, the nozzle can also be adapted to incorporate venting means such as channels running axially along most of the nozzle's length.

The injection moulding apparatus can be equipped with more than one injection head, such as two, which can inject composition simultaneously into the mould or container. Desirably, the composition injected through each injection head is different, for example visually, one being coloured and the other translucent or one being plain and the other marbled, or simply each having a different colour, such as one white and the other blue. This variation can be contemplated particularly when both of the compositions are relatively viscous. Under such conditions, the compositions are relatively viscous at such temperatures and have little opportunity to blend together. It is naturally preferable to select the compositions so that both will have similar viscosities under the prevailing conditions. By employing more than one nozzle or a divided nozzle, it is possible to produce soft solids having stripes, especially if the nozzles and mould/container are moved axially relative to each other during the filling operation. Rotation of the heads about the axis of the container/mould can result in a swirl/stripe effect. Where the nozzle tips from the heads are concentrically positioned, a bulls-eye design can be achieved.

Soft Solid Formulations

Suitable deodorant or antiperspirant compositions for employment in the present invention can include the following ingredients, %s herein being by weight based on the composition unless otherwise stated.:

A) Antiperspirant and/or Deodorant actives
   Ai) Antiperspirant actives, preferably in an amount of from 0.5–60%, particularly from 5 to 40% and especially from 10 to 35%.
   Aii) Deodorant actives, preferably from 0.01 to 20% and particularly from 0.1 to 5% of which at least one of Ai) and Aii) is present
B) Carrier, preferably from 15 to 95% and particularly from 20 to 80%
C) Structurant, preferably from 0.1 to 30% especially at least 0.5% and particularly from 1 to 25%
D) Additives, preferably from 1 to 50% and particularly from 5 to 30%.

Ai) Antiperspirant actives are often selected from astringent active salts, including in particular aluminium, zirconium and mixed aluminium/zirconium salts, including both inorganic salts and organic salts and complexes. Preferred astringent salts include aluminium, zirconium and aluminium/zirconium halides and halohydrate salts, such as chlorohydrates.

Aluminium halohydrates can be represented by the general formula $Al_2(OH)_xQ_y.wH_2O$ in which Q represents chlorine, bromine or iodine, x is from 2 to 5 and x+y=6, x and y being either integers or non-integers and w represents a variable extent of hydration.

Some especially preferred halohydrate salts comprise activated aluminium chlorohydrates such as those described in EP-A-6739 (Unilever N V et al) and other actives are described in EP-A-28853, the contents of both specifications being incorporated herein by reference.

Active zirconium salts can be represented by the following empirical general formula: $ZrO(OH)_{2n-nz}B_z.wH_2O$ in which z is a variable in the range of from 0.9 to 2.0, n is the valency of B, so that the value 2n–nZ is at least 0. B is selected from the group consisting of halides, including chloride, sulphamate, sulphate and mixtures thereof. w represent variable hydration. Preferably B represents chloride and the variable z lies in the range of from 1.5 to 1.87. In practice such zirconium salts are usually not employed by themselves, but as a component of a combined zirconium and aluminium based antiperspirant.

Antiperspirant complexes based on the aluminium and/or zirconium astringent salts can be employed. The complex often employs a chelate comprising a caboxylic acid group, such as an amino acid. Examples of suitable amino acids include dl-trypophan, dl-phenylalanine, dl-valine, dl-methionine and β-analine, and especially glycine ($CH_2(NH_2)COOH$). It is especially desirable to employ complexes of a combination of aluminium halohydrates (particularly chlorohydrates) and zirconium chlorohydrates with amino acids such as glycine, as disclosed in U.S. Pat. No. 3,792,068 (Luedders et al). Certain of those complexes are commonly called ZAG in the literature. ZAG actives generally contain Al, Zr and Cl in an Al:Zr mole ratio from 2 to 10:1, especially 2 to 6:1, an Al:Cl mole ratio from 2.1 to 0.9:1 and a variable amount of glycine. Activated ZAG complexes can be obtained from Summit, Westwood and Reheis.

Other actives which can be used in compositions produced and/or dispensed in accordance with the present invention comprise astringent titanium salts, such as those described in GB-A-2299506.

The proportion of antiperspirant salt in the composition normally includes the weight of any water or complexing agent that may also be present.

The antiperspirant salts are often employed herein in particulate form and usually in compositions that are conveniently referred to as anhydrous or substantially anhydrous. The particle size of antiperspirant salts in such compositions often falls within the range of 0.1 to 200 micrometers. Mean particle sizes for cast processes are often from 3 to 40 μm. The propensity of the particulate salts to segregate increases as the particle size increases. Advantageously, and particularly in the context of dispensing the compositions in an injection moulding process at a temperature in the vicinity of its normal setting temperature, it is possible to employ solids having a larger mean particle size than when similar compositions would be dispensed in a conventional cast process. That is because the selected process conditions minimise or at least ameliorate the likelihood of particle segregation. The benefit of ameliorating particle sedimentation is more readily apparent for larger particle sizes, such as in the region of mean particle sizes of 20 to 100 μm and preferably 20 to 40 μm, or higher. The benefits from lessened sedimentation likewise applies to other particulates to some extent, but is of particular value for actives.

Aii) Herein a deodorant active indicates a material which is capable of killing microrganisms, particularly bacteria, and/or hindering their growth, i.e. including bactericides and bacteristats which either in themselves generate a malodour or which (more typically) promote the decomposition of secreted body oils into malodiferous compounds such as fatty acids. The deodorant actives include the aforementioned antiperspirant actives and additionally other inorganic or organic materials or mixture of organic and inorganic actives. Amongst organic antimicrobial materials, one commonly recognised class comprises short chain monohydric alcohols, often considered to comprise up to 4 carbons, of which ethanol is especially prominent and isopropanol is sometimes employed to replace all or a fraction of the ethanol. A further class comprises bi or polyhydric alcohols such as ethylene glycol or propylene glycol. It will be recognised that the two previous classes of antimicrobial materials can function also as a carrier for other components of the composition.

A still further class of deodorant actives comprises chlorinated aromatics, including biguanide derivatives, of which materials known as Triclosan, Triclorban™ and Chlorhexidine™ warrant specific mention. Yet another class comprises polymeric biguanide salts such as available under the trademark Cosmosil™. These two classes may be employed instead of or in addition to alcohols or polyols, and often in amounts selected in the range of from 0.001 to 1%, and particularly from 0.1 to 0.5% by weight.

Inorganic antimicrobial materials include zinc salts such as zinc oxide, hydroxide, carbonate, phenol sulphonate or ricinoleate, magnesium salts such as magnesium oxide, hydroxide, or carbonate, sodium bicarbonate, rare earth metal salts such as lanthanum oxide, hydroxide or carbonate or combinations of any two or more such salts.

B) The carrier that is incorporated in compositions employed herein comprises one or more liquid materials that is fluid at filling temperatures for the composition and can be gelled or otherwise structured by the structurant or mixture of structurants to provide a soft solid product at use temperature, i.e. typically below 40 and usually below 30° C. Where one or more of the remaining constituents is itself fluid at dispensing temperatures, such as a short chain monohydric alcohol or di or polyol having a melting point of below 40° C., it can provide the carrier function as well and the presence of an additional carrier is optional. The carrier can be hydrophilic or hydrophobic or a mixture of both. In many embodiments, the carrier or a major fraction of the carrier is hydrophobic, generating an oil phase.

Hydrophobic Carriers

One class of carriers that has found particular favour in recent years, and which is particularly desirable in formulations in-line compounded and/or injection moulded in accordance with the present invention, comprises liquid siloxanes and particularly volatile polyorganosiloxanes, i.e. liquid materials having a measurable vapour pressure at ambient conditions. The polyorganosiloxanes can be linear or cyclic or mixtures thereof. Preferred siloxanes include polydimethsiloxanes and particularly those containing from 3 to 9 silicon atoms and preferably not more than 7 silicon atoms. Most preferred polydimethsiloxanes are cyclic containing from 4 to 6 silicon atoms, otherwise often referred to as cyclotetramethicone, cyclopentamethicone and cyclohexamethicone, and mixtures thereof. The volatile siloxanes normally by themselves exhibit viscosities of below 5 to 10 centistokes, and particularly above 0.1 centistokes.

The volatile silicones can also comprise branched linear or cyclic siloxanes such as the aforementioned linear or cyclic siloxanes substituted by one or more pendant —O—Si $(CH_3)_3$ groups. Examples of commercially available silicone oils which are employable include Dow Corning 344, Dow Corning 345 and Dow Corning 244, Dow Corning 245 and Dow Corning 246, and grades of Dow Corning 200 with viscosity of below 10 centistokes (from Dow Corning Corporation) Silicone 7207 and Silicone 7158 (from Union Carbide Corporation) and SF1202 (from General Electric [US]). Volatile silicones are often present in a proportion of from 10 to 90% and in many formulations from 20 to 70%.

The carrier employed in compositions herein can alternatively or preferably additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include grades of Dow Corning 556 and Dow Corning 200 series having viscosities of above 20 centistokes. Non-volatile silicones are often present in not more than about 30% by weight of the composition, and preferably from 1 to 15% by weight. In many instances, when a non-volatile silicone oil is present, its weight ratio to volatile silicone oil is in the range of from 1:3 to 1:100.

Suitable non-silicone organic carriers include liquid aliphatic hydrocarbons such as mineral oils or hydrogenated polyisobutene, often selected to exhibit a low viscosity. A further example of liquid hydrocarbons comprises polydecene and liquid paraffins and isoparaffins containing at least 10 carbons. The liquid hydrocarbons are often present in a proportion of from 0 to 80%, and particularly 0 to 20% by weight.

Other suitable carriers are liquid aliphatic esters containing at least one long chain alkyl group, such as esters derivable from $C_1$–$C_{20}$ alkanols esterified with a $C_8$ to $C_{22}$ alkanoic acid or $C_6$ to $C_{10}$ alkanedioic acid. Suitable aliphatic esters include isopropyl myristate, lauryl myristate, isopropyl palmitate, diisopropyl sebacate and diisopropyl adipate, of which isopropyl palmitate is particularly favoured. Further suitable esters comprise liquid aromatic esters, including fatty alkyl benzoates having a melting point of below 20° C., such as $C_8$ to $C_{18}$ alkyl benzoates. The liquid esters are often present in a proportion of from 0 to 30% by weight.

The carrier can additionally or alternatively comprise liquid aliphatic ethers derivable from at least one fatty $C_8$ to $C_{18}$ alcohol, particularly polyglycol ethers, such as PPG-3 myristyl ether or lower alkyl ethers of polyglycols such as PPG-14 butyl ether.

It will be recognised that when a particulate antiperspirant is employed in such hydrophobic carriers, it will form a suspension unless the formulation additionally contains enough hydrophilic carrier to dissolve all the antiperspirant. The twin srew extruder is particularly suitable for making suspension antiperspirant formulations, normally anhydrous formulations.

Hydrophylic Carriers

The carrier can also comprise one or more glycols such as propylene glycol or dipropylene glycol, for example present in an amount of from 0 to 80%, or a polyol comprising at least three hydric substituents such as glycerol or sorbitol, present in an amount of suitably up to 20%, eg from 0 or 0.5 to 15%, such as up to or around 10% by weight. The polyol can be incorporated advantageously after addition of any particulate antiperspirant and at a temperature that is from about 1 to 10° C., especially 2 to 6° C. above the gelling temperature of the formulation, ie where its viscosity would increase noticeably in the absence of shear mixing. A comparatively high screw speed is desirable, though naturally below that at which shear thinning is evident.

In emulsion formulations, the carrier can be aqueous.

It will be recognised that various of the foregoing carriers can perform one or more beneficial functions in addition to that of providing a liquid carrier for the antiperspirant or deodorant. For example, the liquid paraffins and PPG butyl ether can act as masking agent, various silicone oils act as emollients and glycerol acts as a skin moisturiser.

Mixtures of organic carriers can be employed, as can mixtures of silicone and non-silicone carriers can suitably be employed herein.

The carrier or mixture of carrier employed in the present invention can be and in many effective compositions is anhydrous, i.e. contain no free water.

C) The structurant or structurants that are included in compositions moulded by the processes described herein can comprise organic structurants and/or inorganic thickeners. The choice of structurant normally takes into account the chemical nature of the fluid phase which is being converted to a solid. In the formulations produced herein, the fluid phase to be structured is normally an oil phase, and especially an oil phase containing a silicone fluid, particularly a volatile silicone.

Organic structurants employable herein can be non-polymeric or polymeric. Non-polymeric structurants, including waxes and gellants, are often selected from fatty acids or salts thereof, often containing from 12 to 30 carbons such as stearic acid or sodium stearate, and/or fatty alcohols (typically insoluble in water) often containing from 12 to 30 carbons such as stearyl alcohol. Fatty herein indicates a long chain aliphatic group, such as at least 8 or 12 linear carbons, which is frequently not branched (linear) and is typically saturated, but which can alternatively be branched and/or unsaturated. It is possible for the fatty acid to contain an hydroxyl group, as in 12-hydroxystearic acid, for example as part of a gellant combination, and to employ amido or ester derivatives thereof. Examples of suitable higher molecular weight alcohols include stearyl or behenyl alcohol and sterols such as lanosterol.

Gellant indicates that the material gels the carrier. Other suitable gellants can comprise dibenzoyl alditols, of which a preferred representative comprises dibenzoyl sorbitol. Other organic structurants can comprise hydrocarbon waxes such as paraffin waxes, microcrystalline waxes, ceresin, squalene, and polyethylene waxes (mol weight typically 200 to 10000). Other suitable structurants are waxes derived or obtained from plants or animals such as hydrogenated castor oil (castor wax), carnabau, spermacetti, candelilla, beeswax, modified beeswaxes, and Montan wax and individual waxy components thereof. Such waxes often comprise a mixture of waxy components including one or more of fatty alcohols and esters, fatty acids and esters, and hydrocarbons such as paraffins. The waxes from some plants comprise fatty ester derivatives of polyols, such as glycerol. Mono and especial di and triglycerides are often very desirable. Synthetic glycerides can be obtained in various grades of Synchrowax™. A combination of glycerides alleged to have desirable properties comprises a mixture of behenate and C18 to C40 non-behenate glycerides (20:1 to 1:1).

It is especially suitable herein to employ a wax structurant or mixture of wax structurants. Mixtures of the organic structurants can be employed, such as mixtures of a fatty acid/salt with a wax. Suitable choice of mixtures of structurants can reduce the visibility of antiperspirant/ deodorant composition deposited in use on the skin. Wax structurants are typically present in an amount of from 5 to 20% by weight when present as a principal structurant and in lower amounts such as up to 6% when present in a supplementary role.

Some suitable structurants form a fibrous network, such as selected n-acyl amino acid derivatives, including ester and amide derivatives, such as N-Lauroyl-L-glutamic acid di-n-butylamide, either by itself or when contemplated in conjunction with hydroxystearic acid or an ester or amide derivative thereof. Still further gellants include amide derivatives of di or tribasic carboxylic acids, such as alkyl N,N' dialkylsuccinimides, eg dodecyl N,N'-dibutylsuccinimide.

Yet further fibre forming structurants comprise a combination of oryzanol and β sitosterol, preferably in a mole ratio range of from 3:2 to 2:3, or polyacylated cellobiose, especially cellobiose nominally fully esterified with C8 to C10 linear aliphatic carboxylic acids. Esterified cellobiose can be produced by following a method for esterifying saccharides described by Tanaka et al in Liquid Crystals, 1995 Vol 19 pages 441–448. Such latter two classes of structurants are the subject of copending applications. Yet a further structurant described in a copending application comprises certain phenyl derivatives of threitol or tartaric acid. Threitol derivatives can be made a process according to Kataky et al, J Chem Soc Perkin Trans vol 2 p521 (1990) and tartrate derivatives by Hiu et al in J Chem Csoc Vol 118, 4550 (1996).

Polymeric gellants which can be employed can comprise organo polysiloxane elastomers such as reaction products of a vinyl terminated polysiloxane and a cross linking agent or alkyl or alkyl polyoxyalkylene-terminated poly(methyl substituted) or poly(phenyl substituted) siloxanes. Other polymeric gellants can comprise polyacrylamides, optionally polysiloxane/polyamide copolymers.

Fibre forming or polymeric structurants are often employed in an amount of from 1 to 15% by weight.

It is often convenient to employ a polymeric thickener such as ester derivatives of polysaccharides or cellulosic materials, and in particular fatty acid esters of polysaccharides such as dextrin. The fatty acids are advantageously from C12 to C18 aliphatic acids, such as palmitic acid, and the dextrin polysaccharide backbone commonly contains from 10 to 50 repeat units. Examples are commercially available under the trade name Rheopearl. Other examples of polymeric thickeners include polyamides available under the mark Versamid 950. Yet further thickeners styrene/ alkylenbe block copolymers under the mark Kraton G, or styrene copolymers under the mark Kristalex. The proportion of thickening polymer is often chosen in the range of from 2 to 10%, and in many instance from 3 to 7% by weight.

Where a significant fraction of the carrier in the composition comprises a monohydric alcohol and/or a di or polyol, it can be convenient to employ as thickener, at least in part, a dibenzoyl derivative of a saccharide, and especially dibenzoyl sorbitol.

Where the composition comprises as a significant fraction of the carrier a volatile silicone, it can be preferable to employ a silicone elastomer and in particular a crosslinked polyorganosiloxane, often particulate, obtained by crosslinking a vinyl terminated siloxane polymer or by otherwise introducing cross linking. In operation, the particulate polyorganosiloxane absorbs the volatile silicone and is conveniently employed in a weight ratio to the volatile silicone of from 1:3 to 1:20. The elastomer is preferably used to supplement a primary structurant to obtain a beneficial combination of effects.

Inorganic thickeners are often selected from siliceous and alumino-siliceous materials including silicas and clays. Many inorganic thickeners comprise a particulate colloidal silica, usually having a small particle size, such as below 1 μm. When used as the primary thickener, it is normally present in an amount of at least 3% by weight and particularly 4 to 7% by weight. It can be used as a supplementary thickener in lower amounts such as up to 3% by weight.

Clays and silicas can also function as suspending or bulking agents. Examples of suitable silicas include fumed silicas. Suitable clays include bentonites, hectorites and colloidal magnesium aluminium silicates. Commercially available clays are available under the trademarks Veegum and Laponite. It is preferable to include montmorillonite clays which have been hydrophobically surface treated, for example by reaction with an amine. Preferred hydrophobic-treated clays are available under the Trademark Bentone (various grades).

Additional bulking agents/fillers which can be contemplated include particulate fillers including talc, sodium bicarbonate, starches, including corn starch, modified starches and mixtures thereof. The amount of such additional fillers/bulking agents is often not more than 15%, and preferably up to 10% such as 1 to 5% by weight.

D) For improving the consumer-perceived properties of the soft solids, it may be desirable to incorporate additives into the formulation. Such additives can include fragrances and skin benefit agents. Skin benefit agents are products which will be deposited onto the skin when the deodorant or antiperspirant composition is applied to the skin and which will impart to or maintain desirable properties for the skin.

It is particularly preferred in some embodiments of the invention that the deodorant or antiperspirant compositions comprise skin benefit agents such as, for example, moisturising components. The benefit agent may exist as a single component phase or, more commonly, is miscible with some of the ingredients of the formulation, such as the oil phase, thereby usually contributing the overall carrier content of the formulation.

The process of the invention is particularly suitable for the incorporation of benefit agents into a deodorant or antiperspirant composition, and in particular when the deodorant or antiperspirant composition is below its melt temperature. Preferably, benefit agent is added to the deodorant or antiperspirant composition in the means for feeding the deodorant or antiperspirant composition to the dispensing means.

Where said means for feeding the deodorant or antiperspirant composition comprises a screw feed, the benefit agent may be added at any suitable position along the screw feed. Using the equipment of the present invention, where a temperature profile exists in the equipment, it is possible to control the temperature at which the benefit agent is added. It is therefore possible to introduce the benefit ingredient into a bulk flow of chosen viscosity. By using appropriate equipment and processing parameters, for example by appropriate temperature control, it is also possible to introduce the benefit agent into a bulk flow of material which has a chosen level of mixing and structuring.

Benefit agents include components which moisturise, condition or protect the skin. Suitable benefit agents include moisturising components, such as, for example, emollient/oils. By emollient oil is meant a substance that softens the skin and keeps it soft by retarding the decrease of its water content and/or protects the skin. A significant proportion of skin benefit agents also are capable of providing other functions to the composition. Thus, many comprise oils which can act as carriers. Others are waxes and fatty acids or alcohols which can provide structure to an oil phase, either alone or in conjunction with other materials. It will be recognised from their description which other function they provide or contribute to.

Benefit agents also include wash-off agents incorporated to facilitate the removal of the antiperspirant or deodorant composition from human skin by washing with water. Such agents can be selected from non-ionic surfactants and particularly nonionic ester or ether surfactants comprising a polyoxyethylene moiety, often containing from about 2 to 80, and especially 5 to 60 oxyethylene units and a hydrophobic alkyl, alkenyl or aralkyl moiety, normally containing from about 8 to 50 carbons and particularly from 10 to 30 carbons. Such non-ionic surfactants can also be derived from a polyhydroxy compound such as glycerol. Examples of agents which offer wash-off benefits include ceteareth-10 to -25, ceteth-10 to -25, steareth-10 to -25, and PEG-(15- to -25)-stearate or distearate, Preferred benefit agents include:

Silicone oils, including polysiloxanes and siliconols; amino, alkyl, alkylaryl and aryl silicone oils. The silicone oil used can sometimes have a viscosity in the range 100 to 100,000 centistokes. The silicone oils can be either volatile oils, non-volatile oils or a mixture of both.

Low melting point silicone waxes, eg SF1642: these can also contribute to structuring the composition.

Fats and oils including natural fats and oils such as jojoba, soyabean, rice bran, avocado, almond, olive, sesame, persic, castor, coconut, mink, arachis, corn, cotton seed, palm kernel, rapeseed, safflower seed and sunflower oils; cocoa butter, hardened oils obtained by hydrogenating the aforementioned oils; and synthetic mono, di and triglycerides such as myristic acid glyceride and 2-ethylhexanoic acid glyceride;

Hydrophobic plant extracts;

Higher alcohols and fatty acids such as behenic, palmitic and stearic acids; lauryl, cetyl, stearyl, oleyl, behenyl, cholesterol and 2-hexadecanol alcohols;

Esters such as cetyl octanoate, cetyl lactate, myristyl lactate, cetyl palmitate, butyl myristate, butyl stearate, decyl oleate, cholesterol isostearate, myristyl myristate, glyceryl laurate, glyceryl ricinoleate, glyceryl stearate, alkyl lactate, alkyl citrate, alkyl tartrate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, isopropyl adipate, propylene glycol monolaurate, propylene glycol ricinoleate, propylene glycol stearate, and propylene glycol isostearate;

Essential oils such as fish oils, mentha, jasmine, camphor, white cedar, bitter orange peel, ryu, turpentine, cinnamon, bergamot, citrus unshiu, calamus, pine, lavender, bay, borage, clove, hiba, eucalyptus, lemon, starflower, thyme, peppermint, rose, sage, menthol, cineole, eugeniol, citral, citronelle, borneol, linalool, geraniol, evening primrose, camphor, thymol, spirantol, pinene, limonene and terpenoid oils;

Lipids such as cholesterol, ceramides, sucrose esters and pseudo-ceramides as described in EP-A-556 957;

Vitamins such as vitamin A and E, and vitamin alkyl esters, including those vitamin C alkyl esters;

Suncreens such as octyl methoxyl cinnamate (Parsol MCX) and butyl methoxy benoylmethane (Parsol 1789);

Phospholipids; and

Mixtures of any two or more of the foregoing skin benefit agents. It will be recognised that a number of the materials encompassed herein with the term skin benefit agents can contribute to the provision of other functions.

The skin benefit agent such an emollient/oil is generally used in an amount from about 1 to 20%, preferably 1 to 15% by weight of the composition.

Other beneficial agents which can be incorporated comprise an anti-oxidant. Suitable examples include free radical inhibitors such as alkyl phenols e.g. butyl hydroxytoluene or ascorbic acid.

The compositions desirably, though not always, contain at least one perfume, which normally is incorporated within an oily phase in the composition, and typically is present in an amount of from 0 to 5% w/w, and in many instances from 0.2 to 2.5% w/w. The perfume can be introduced in its natural form, i.e. normally as an oil, or it can be wholly or partially encapsulated.

In those aspects of the present invention employing injection of the formulation into a dispensing container, it is particularly desirable for the formulation to contain not more than 50% by weight of solid particulate material, which in practice is dispersed in a fluid carrier above its solidification temperature. Such solid particulate material is normally considered to include one or more of antiperspirant active, and/or filler such as talc, clay or silica. It is typically inorganic, though the antiperspirant can contain an organic complexing agent. In many instances the proportion of particulate material is in the range of 0 to 35% by weight, and for antiperspirant formulations, especially 15 to 35% by weight. As used herein, the term particulates does not include organic gellants or waxes, but does include inorganic thickeners.

An optional further component can comprise a dispersed phase within the carrier. Normally, this will be aqueous, though may constitute an alternative hydrophilic liquid. The dispersed phase will usually comprise from 0 to about 85% of the formulation and often from about 30 to 80% in water in oil emulsions. In such formulations, the antiperspirant active and similarly water-soluble materials are dissolved to at least a considerable fraction in the aqueous phase. The present invention will be further described by way of the accompanying drawings.

When the formulation is in the form of an emulsion, it normally includes at least one emulsifier, such as a nonionic surfactant or mixture having an average low HLB value, such as up to about 10, often 3 to 8. The proportion of emulsifier(s), in such an emulsion is often selected in the range of from 0.1 to 10% w/w, and in many instances from 0.25 to 5% w/w.

Many suitable emulsifiers are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditols as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil sunflower seed oil or soya bean oil. Such non-ionic surfactants can also be derived from a polyhydroxy compound such as glycerol or sorbitol or other alditols. Examples of emulsifiers include ceteareth-10 to ceteareth-25, ceteth-10 to ceteth-25, steareth-10 to steareth-25, and PEG-15 through to PEG-25 stearate or distearate. Other suitable examples include C10–C20 fatty acid mono, di or tri-glycerides. Further examples include C18–C22 fatty alcohol ethers of polyethylene oxides (8 to 12 EO).

The co-emulsifiers, which typically have a low HLB value, and often of from 2 to often comprise mono or possibly fatty acid diesters of polyhydric alcohols such as glycerol, sorbitol, erythritol or trimethylolpropane. The fatty moiety is often from C14 to C22 and is saturated in many instances, including cetyl, stearyl arachidyl and behenyl. Examples include monoglycerides of palmitic or stearic acid, sorbitol mono or diesters of myristic palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in C1 to C12 alkyl groups.

When the formulation is in the form of an emulsion, it has been observed as being more sensitive than suspension formulations to shear effects, so that it is preferable to fill the dispensing container at a temperature that is not excessively below its normal setting temperature, such as not more than about 5° C. below. If a temperature of between 5 and 10° C. below its normal setting temperature is employed, it is preferable to employ particularly low shear mixing conditions.

DETAILED DESCRIPTION OF DRAWINGS

Figure 1:
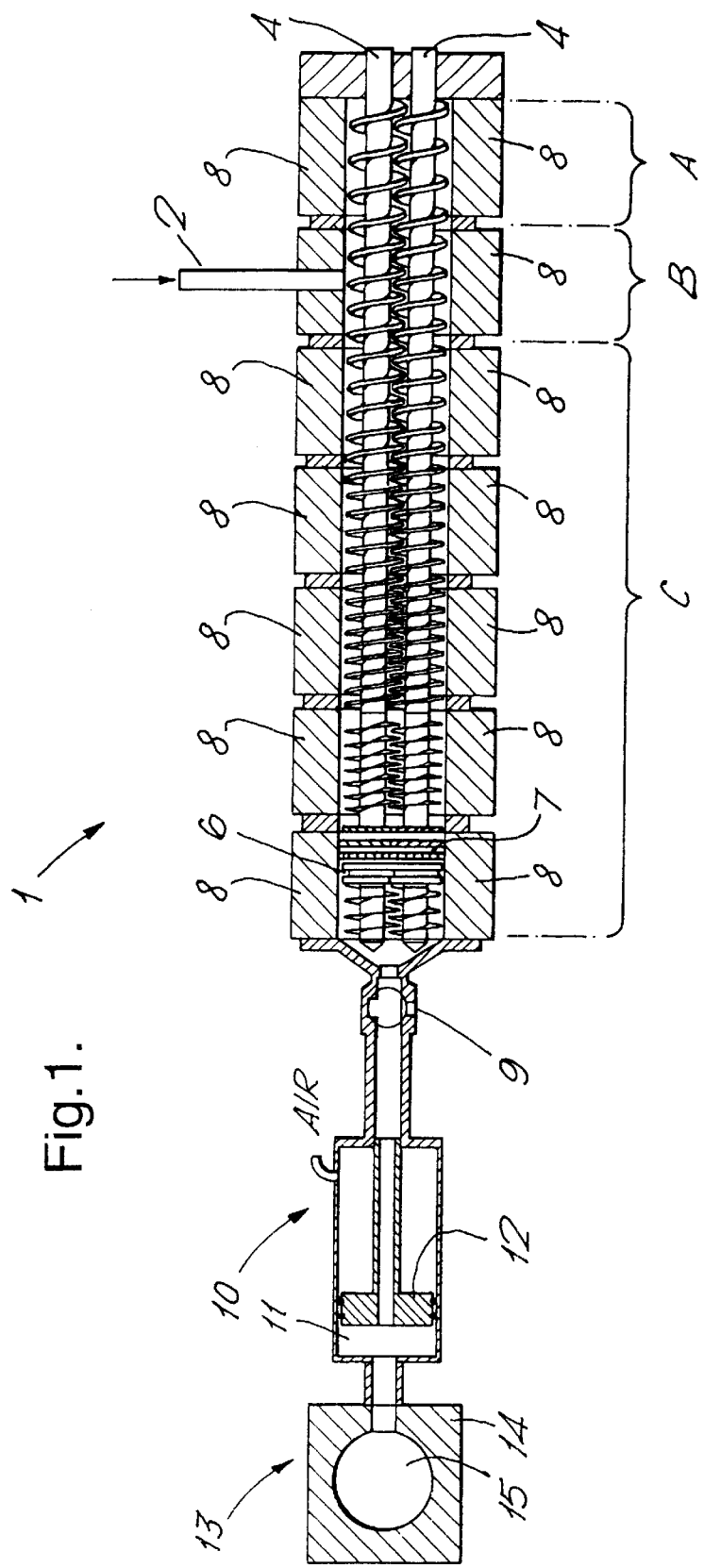
FIG. 1 shows apparatus for use in the method of the invention (plan view, twin-screw extruder).

FIG. 1 shows a plan view of one embodiment of the present invention comprising a twin screw extruder and an injection moulding apparatus. It is generally designated (1). The apparatus (1) is suitable for feeding deodorant or antiperspirant composition which is supplied in molten form. A duct (2) is provided for receiving a feed of liquid deodorant or antiperspirant composition, for example from a prior step in the manufacturing process (not illustrated). The duct (2) feeds into a jacketed element (8) adjacent to one end of an extruder (3). In the extruder (3) there are two intermeshing, co-rotating feed screws (4), (5). At the end of the screws distant from duct (2), a set of medium shear mixing elements is provided, comprising three tri-lobe paddles (6) and three 'melting discs' (7) to provide back pressure and some mixing. Temperature control means are provided in jacketed elements (8) around the barrel of the extruder (3). The temperature control means comprise channels for liquid coolant, and electrical units for heating. The extruder (3) is divided into three zones, A, B and C. Temperature control means in zone A of the extruder are maintained at a low temperature, e.g. 30° C., to encourage the formation of solid deodorant or antiperspirant composition to seal the end of the shafts of the screws (4),(5). The temperature control means in the elements (8) in the zone marked B are at high temperature to maintain the deodorant or antiperspirant composition in fluid state to prevent blockages at the feed point of duct (2). The temperature control means in the elements (8) in the region marked C (i.e. the remainder of the extruder length) are for conditioning the deodorant or antiperspirant composition progressively to the desired temperature for filling.

At the outlet of the extruder (3), there is provided an in-line three-way valve (9), which can be used for sampling and recycle. When this valve is in the straight-through position, it is in fluid connection with an accumulator (10) comprising a cylindrical chamber (11) and a piston (12).

The position of the accumulator piston (12) in the cylinder (11) varies according to the flow of material into and out of the accumulator. The accumulator (10) is in fluid connection with an injection head (13) comprising an injection chamber (14) which comprises a cylinder with a retractable piston (15). The injection head (13) has a nozzle (not illustrated in this Figure) which will be described in relation to FIG. 2 below. Pneumatic pressure behind the accumulator piston (10) keeps material in the accumulator (10) at constant pressure and provides a buffer between the continuous flow from the extruder (3) and the intermittent demands of the injection head (13). The three-way valve (9) and accumulator (10) are provided with temperature-controlled jackets.

In operation, a molten feed of deodorant or antiperspirant composition at a temperature above its melting point is fed through duct (2) and forced by the co-rotating screws (4),(5) in the direction of the solid-headed arrow through the connection (9) into the accumulator (10). The accumulator stores the material outletting from the extruder (3) and intermittently feeds it to the injection head (13) as demanded. Its temperature on reaching connection (9) is close to its regular setting temperature. During the first phase of injecting the material into a barrel for soft solid (not illustrated), deodorant or antiperspirant soft solid material is accumulated in the accumulator (10) the material then flows into the injection chamber (14) as the piston (15) is displaced upwards. When a predetermined volume of deodorant or antiperspirant composition has been accumulated under the piston (15), the piston (15) is actuated downwardly by hydraulic pressure (not shown) whereby pressure is applied to the deodorant or antiperspirant composition within chamber (14) which is forced through the nozzle into the barrel (neither illustrated).

Figure 2:
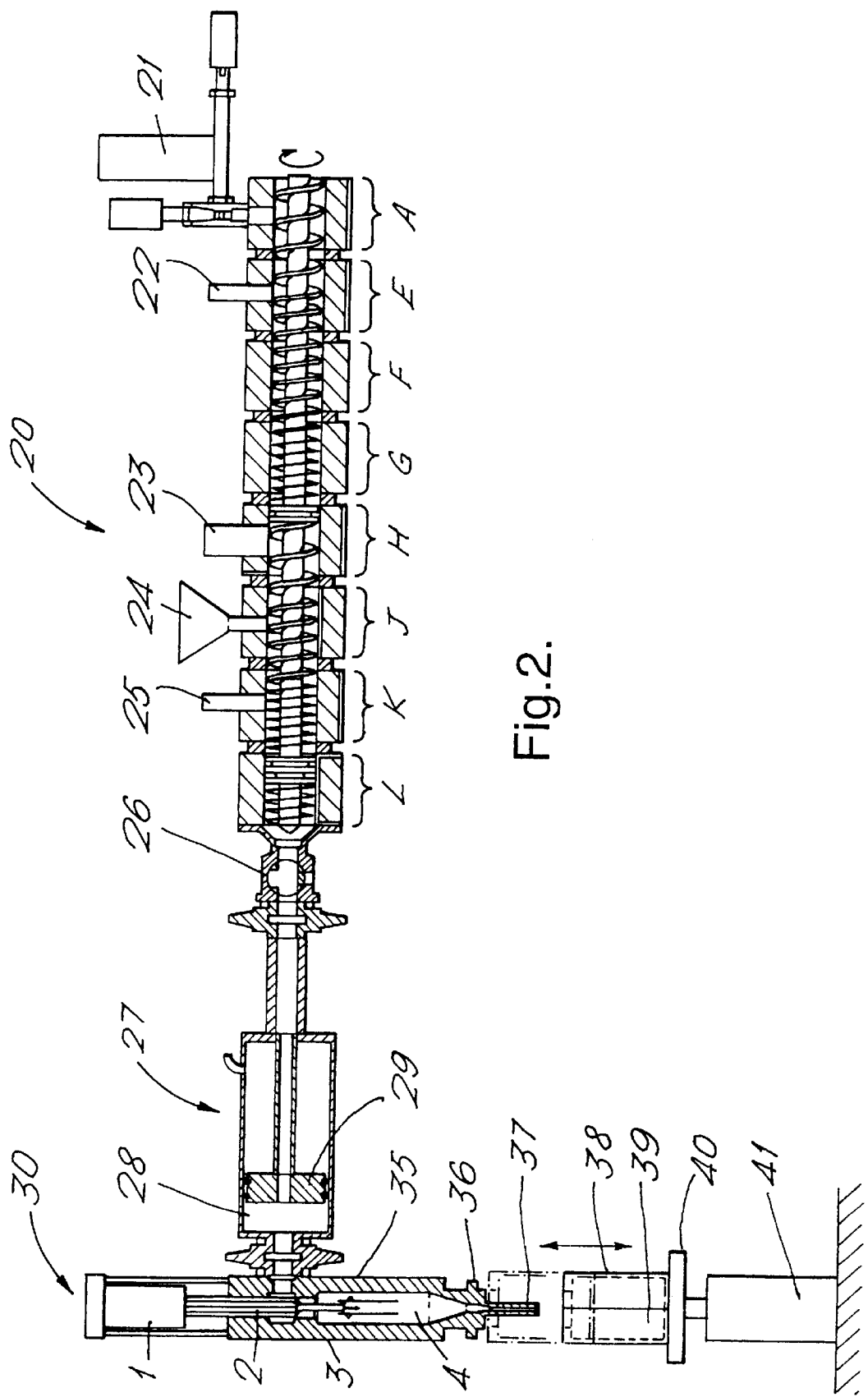
FIG. 2 shows a further apparatus in accordance with the present invention suitable for in-line compounding (side view, twin-screw extruder with in-line low shear injection head, degassing zones and solid-feed stuffer).

FIG. 2 shows a side view in cross section of an embodiment of the present invention suitable for in-line compounding. The apparatus comprises an extruder (20), with two intermeshing, co-rotating feed screws, each with a single flight as described in FIG. 1. The general configuration of the two intermeshing screws can be chosen to suit the particular application. At the end of the screws, a set of medium shear mixing and kneading elements is provided also as described in FIG. 1. The mixing and kneading elements can be interspersed between conveying screw elements of various pitch. Temperature control means, comprising channels for liquid coolant and electrical heating means, are provided by jacketed elements around the barrel of the extruder (as in FIG. 1).

The apparatus can accept liquid, semi-solid or solid materials as feed, depending on the feeding arrangement chosen. Particulate material such as structurant is fed into zone A of the extruder (20) via a solid feeder (21). Fluid materials are fed into zone E of the extruder (20) by a liquid feeding means (22). A degassing port (23) is illustrated in zone H of the extruder (20). At zone J of the extruder (20), a solid feeding means (24) for delivering solid deodorant or antiperspirant active or filler or adjuncts to the extruder is illustrated. At zone K, a duct (25) is shown for the introduction of liquid additives by a pump (not shown). Since the extruder zones can be interchanged, it should be understood that solids, liquids, and additive feeds may be introduced at any position along the length of the screw. One or a number of feeds may be supplied for a particular product.

At the exit of the extruder, is a three-way valve (26) used for sampling and recycle. When this valve is in the straight-through position, conditioned material from the extruder passes into an accumulator (27) comprising a cylindrical chamber (28) and an accumulator piston (29). The position of the piston (29) in the cylinder (28) varies according to the flow of material into and out of the accumulator. A pneumatic pressure behind the piston keeps material in the accumulator at constant pressure and thus provides a buffer between the continuous flow from the extruder (20) and the intermittent demands of the injection head (30). The three-way valve (26) and accumulator (27) are provided with temperature-controlled jackets.

The injection head (30) is positioned perpendicular to the extruder (20), with its axis vertical. It is provided with a means for temperature control (not shown).

The injection head (30) comprises a hydraulic actuator (31), a spindle (32) connected to the actuator, an inlet chamber (33), an injection chamber (34), a non-return ring check valve (35) and an injection valve (36). Also shown is the nozzle (37) and the dispensing container (38) to receive the composition. The nozzle (37) and dispensing container (38) can be pre-heated before injection, if required.

In charging mode, the injection valve (36) is closed. The pressure above the ring check valve (35) is greater than that below, and the valve moves to its lower seat. In this position material can flow through the ring check valve (35), between the injection spindle (32) and the cylinder wall. As the injection spindle (32) is moved hydraulically upwards by the movement of the actuator, prepared fluid material flows into the injection chamber (34). The charging process is complete when the spindle (32) is fully up.

The spindle diameter is minimised (within constraints of mechanical strength) to give maximum area for flow, and therefore exert minimal extensional shear on the flowing material.

When the pressure below the ring check valve (35) exceeds that above, the valve moves to its upper seat and isolates the injection chamber (34) from the inlet chamber (33). At this point the machine is charged for injection. This passive valve system removes the need for an inlet control valve, and provides for first-in first-out material flow to the dispensing container (38).

In injection mode, the nozzle (37) extends into the cavity (39) of the dispensing container (38) through its open top. The dispensing container (38) is mounted on a plate (40), which is movable up and down by a hydraulic system (41) or manually, the injection valve (36) is opened the cylinder (31) is hydraulically driven downwards and the pressure in the injection chamber rises to above that in the inlet chamber. This closes the ring check valve (35). As the spindle (32) moves downwards with the actuator, material flows from the injection chamber through the open injection valve and into the dispensing container via the nozzle (37).

The rate of advance of the spindle (32) is linked to the rate of retraction of the plate (40). As a result, the dispensing container (38) drops as the cavity (39) is filled with deodorant or antiperspirant composition. The deodorant or antiperspirant composition flowing under pressure tends to fill the bottom upwards of the cavity (39). The rate of retraction of the plate (40) is adjusted so that the tip of the nozzle (37) is always just below the surface of the deodorant or antiperspirant composition in the cavity (39). This gives good fill quality.

Alternatively, equally good fill quality is obtained by moving the nozzle (37) instead of the plate (40). The nozzle is moved to the base of the mould cavity (39) and raised out of the barrel as the mould cavity (39) is filled with deodorant or antiperspirant composition.

The volume of material delivered to the dispensing container is determined by the stroke of the hydraulic actuator. The velocity of the material as it is delivered to the dispensing container is determined by the hydraulic pressure.

The apparatus according to FIG. 2 is capable of generating an applied pressure in the injection head which is between 105 kPa and 6000 kPa.

The present invention will be further described by way of the following non-limiting examples:

EXAMPLES

Example 1

In Example 1, antiperspirant soft solid product of Formulation A summarised below was prepared employing apparatus according to FIG. 1, a Betol co-rotating twin screw extruder, having 30 mm diameter screws and eight temperature control zones leading via a connection valve to piston-type injection unit in which the connection valve and injection head were also temperature controlled. In this example, the extruder acted to transport the fluid antiperspirant composition to the injection unit.

| Formulation A | |
|---|---|
| Constituent | % by weight |
| Cyclomethicone (DC345) | to 100% |
| Hydrogenated castor oil and Silicone wax (GE 1642) | 10–12 |
| Emollient oil (Silkflo 364 NF) | 12–16 |
| Al-Zr antiperspirant active | 23–25 |
| Talc | 4–8% |

| -continued | |
|---|---|
| Formulation A | |
| Constituent | % by weight |
| Suspending agent Bentone 38 clay) | 1 |
| Perfume | 0.5–2% |

A batch of a composition within Formulation A was prepared in conventional equipment to produce a solid mass and subsequently melted in a conventional stirred heating-jacketed vessel. It was maintained at a temperature of approximately 65 to 70° C. and fed in the form of a fluid mass via a metering pump into the Betol extruder. Zone A was controlled to about 30° C., in order to generate a solid block of material to minimise loss of the composition. In zone B of the extruder, the temperature was controlled at approximately 80° C., which resulted in complete melting of the waxes in the Formulation. The molten mass was conveyed through zone C by the screws rotating at rates of from 66 to 400 rpm, and cooled to a temperature selected in the range of from 45 to 68° C., at which it was fed into the injection moulding unit.

In the Examples herein, the injection pressure in the injection unit was adjusted to within the range of 1000 to 1500 kPa unless otherwise stated.

Creamy soft solid products were obtained under all conditions tested. A groove test was carried out by forming a groove on the top surface of the formulation, storing the formulation at ambient and monitoring the groove visually, to see whether or the extent to which a pool of carrier fluid formed in the groove. In the groove test, no significant pool of fluid was observed after 24 hours storage, indicating that the products of this Example did not suffer significantly from the problem of syneresis.

A cast process for this formulation was carried out at about 56 to 58° C., employing material processed in the same twin screw extruder under the temperature profile and screw conditions described previously in this Example fas feedstock to the Betol injection moulding apparatus. Cast filling at a lower temperature has been observed to block the filler nozzles giving inaccurate fill and the need to rework the product. Product that had been injection moulded at a temperature of 45° C. was obtained having a significantly higher viscosity, not only immediately after filling but also after 24 hours storage when the formulations had cooled to ambient. This not only demonstrates that a pressure injection technique is not only capable of filling over a wider temperature range than a cast technique, but is also able to achieve a higher viscosity from the same concentration of structurant.

The rheology profile of the formulation was tested using a Carri-Med CSL rheometer with a van and measuring cup system. The products having the highest viscosity/shear stress profile were obtained using the higher screw rotation speeds, viz from 200 to 400 rpm.

Example 2

In this Example, apparatus in accordance with FIG. 1 and substantially as described in Example 1, was employed to produce soft solid product from a composition within Formulation B. The screw extruder was operated over a range of from 100 to 400 rpm.

Formulation B

| Constituent | % by weight |
| --- | --- |
| Cyclomethicone (DC245) | to 100% |
| Hydrogenated castor oil | 5 |
| Silicone wax (GE 1642) | 6 |
| Emollient oil (Finsolv TN) | 12–16 |
| AACH antiperspirant active | 23–25 |
| Talc | 4–8% |
| Suspending agent Bentone 38 clay) | 1 |
| Perfume | 0.5–2% |

The composition was injected into the dispensing containers at a temperature controlled to within the range of 35 to 54° C. The Theological properties of the products were assessed after they had cooled to ambient temperature. It was found that the products had very similar properties at both extremes of temperature of injection employed, showing that the injection moulding system is very tolerant of changes in the temperature of injection. A screw speed of 200 to 400 rpm obtained product having the best rheological properties. All the injection moulded products by the groove test did not suffer from synersesis losses. By comparison it was found that the composition which was produced in the extruder could be filled in a cast technique into the dispensing canisters at 50° C., but was unable to be filled by the same technique at 45° C. This confirms that the injection technique was able to operate over a wider temperature range.

Example 3

In this Example, a pre-manufactured composition within Formulation C as shown below was conveyed via a twin screw extruder to an injection unit and injected into a dispensing barrel using the process described below.

Formulation C

| Constituent | % by weight |
| --- | --- |
| beeswax and fatty alcohol structurants and nonionic PEG ester emulsifier | 12 to 15 |
| aqueous ACH antiperspirant active (50% solution) | 20 to 35 |
| benefit agents - (White pigment, sunscreen, stabiliser, mineral oil) | 1.5–3 |
| Perfume | 1–1.5 |
| water | balance |

In this Example, a product was made employing apparatus according to FIG. 2 and comprising a Werner & Pfleiderer co-rotating twin screw extruder having a plurality of temperature control zones, feeding an injection moulding apparatus having a low shear in-line injection head. The extruder had 30 mm diameter screws rotating at rates controlled within the range 100 to 500 rpm. In this Example, the extruder acted to transport the composition, subject it to low shear mixing and feed it to the injection unit.

The pre-formed mixture was rendered mobile by preheating it to 70° C. and feeding it via a gear pump into segment A. Segment A was controlled at 40° C. and the segments were then progressively cooler until the final segment had the intended temperature for injection of either 25 or 30° C. The injection pressure was monitored and peaked at 1150 kPa.

A creamy soft solid was obtained by injection at a temperature of between 25 and 35° C. Product having a viscosity of initially around 30000 cP (milliPas) was obtained at 35° C. Some sensitivity to shear breakdown of structure was observed in product cooled to an injection temperature of 25° C., so that product having higher viscosity, of over 20000 cP (milliPas) both initially and after 24 hours maturing, was obtained at screw speeds of 150 to 250 rpm.

Viscosities in the Examples herein were measured using a Brookfield T bar viscometer, at 20 rpm at ambient temperature (about 23° C.), using spindle D E or F in accordance with the expected viscosity, unless otherwise stated.

Example 4

In this Example, a premanufactured composition within Formulation D as shown below was conveyed via a twin screw extruder to an injection unit and injected into a dispensing barrel using the process described below.

Formulation D

| Constituent | % by weight |
| --- | --- |
| Cyclomethicones (DC245) | balance |
| Dimethicone (DC200/10) | 5 |
| Behenate triglyceride structurant (Synchrowax HR-C) | 5 |
| C18-40 carboxylic acid triglyceride structurant (Synchrowax HGL-C) | 1.25 |
| AZAG antiperspirant active (Q57167) | 25 |
| Perfume | 1 |

In this Example, a product was made employing apparatus according to FIG. 2 and comprising a Werner & Pfleiderer co-rotating twin screw extruder having a plurality of temperature control zones, feeding an injection moulding apparatus having a low shear in-line injection head. The extruder had 30 mm diameter screws rotating at rates controlled at 100 150 or 250 rpm. In this Example, the extruder acted to transport the composition, subject it to low shear mixing and feed it to the injection unit.

The pre-formed mixture was rendered mobile by preheating it to about 65° C. and feeding the molten material via a holding tank held at about 70° C. and a metering pump into segment A. The segments were then progressively cooler until the final segment had the intended temperature for injection. Three injection temperatures were employed, namely 45° C., 55–58° C. and 65° C. The material injected at 45° C. was very viscous and on cooling produced a product having the lowest viscosity which did not increase substantially on cooling, indicating that the material had been subjected to some structural impairment. This viscosity was still 200000 cP (milliPas) indicating that as acceptably viscous soft solid was obtained. The material injected at both 55–58 and 65° C. produced product and conveyed at a three screw speed of 100 rpm on cooling showed viscosities of over 400000 cPs and thickened further with the passage of time. At the higher screw speeds, the viscosity was initially lower, but recovered to over 400000 cP (milliPas) within 24 hours storage indicating that no significant structural impairment had occurred.

Example 5

In this Example, a pre-manufactured composition within Formulation E as shown below was conveyed via a twin screw extruder to an injection unit and injected into a dispensing barrel using the process described below.

| Formulation E | |
|---|---|
| Constituent | % by weight |
| Cyclomethicones (DC245) | balance |
| Dimethicone (DC200/350) | 5 |
| Fumed Silica structurant (Aerosil 200) | 4 |
| propylene carbonate | 0.5 |
| Polyethylene powder (Acumist B18) | 5.5 |
| AZAG antiperspirant active (Q57167) | 24 |
| Perfume | 1 |

In this Example, a product was made employing apparatus according to FIG. 2 and comprising a Werner & Pfleiderer co-rotating twin screw extruder having a plurality of temperature control zones, feeding an injection moulding apparatus having a low shear in-line injection head. The extruder had 30 mm diameter screws rotating at rates controlled at screw speeds of from 100 to 500 rpm. In this Example, the preformed mixture (at ambient temperature) was pumped into the screw extruder using a monopump, and the extruder acted to transport the composition, subject it to low shear mixing and feed it to the injection unit. The segments in the screw extruder were kept at approximately 25° C.

Glossy products were obtained having a creamy appearance. The material was acceptably viscous on injection and increased to between 100000 and 200000 cP (milliPas) on storage for 1 or 2 days. the viscosities after 1 & 2 days were measured at a stirrer rate of 10 rpm.

Example 6

In this Example, a composition within Formulation E as shown above was compounded in line using the twin screw extruder of Example 5 and conveyed to the injection unit of Example 5 and injected into a dispensing barrel using the process described below.

The segments of the screw extruder were maintained at about 25° C. The extruder was operated at rotations of from 100 to 500 rpm. The liquid ingredients were introduced via a metering pump into segment A, the silica thickener into segment C and the antiperperspirant active, and other solids using a loss in weight feeder (K-tron) into segment E.

A creamy product was obtained. At low screw speeds, limited separation of the product was observed and at very high screw speeds a very viscous material was obtained, though it was still injectable to provide a product having a comparable viscosity to product obtained using pre-formed material of Example 5. The best manufacturing conditions employed a screw speed of from 200 to 300 rpm.

Example 7

In this Example, a premanufactured composition within Formulation F as shown below was conveyed via a twin screw extruder to an injection unit and injected into a dispensing barrel using the process described below.

| Formulation F | |
|---|---|
| Constituent | % by weight |
| cyclomethicone (DC245) | balance |
| Silicone elastomer/cyclomethicone (DC JK301) | 30–35 |
| Hydrogenated castor oil | 4–6 |
| Emollient oil (Silkflo 364 NF) | 12–16 |
| Al-Zr antiperspirant active | 23–25 |
| Talc | 4–8% |
| Suspending agent Bentone 38 clay) | 1 |
| Perfume | 0.5–2% |

In this Example, a product was made employing apparatus according to FIG. 2 and comprising a Werner & Pfleiderer co-rotating twin screw extruder having a plurality of temperature control zones, feeding an injection moulding apparatus having a low shear in-line injection head. The extruder had 30 mm diameter screws rotating at rates controlled at 100 to 250 rpm. In this Example, the extruder acted to transport the composition, subject it to low shear mixing and feed it to the injection unit.

The pre-formed mixture was rendered mobile by feeding the material at ambient temperature via a Moyno pump into segment A which was heated to over 70° C. and began the task of rendering it mobile. The segments were then progressively controlled until the final segment had the intended temperature for injection. The injection temperatures were employed, in the range of 58° C. to 70° C. The products obtained had viscosities in excess of 2000000 cP (milliPas) increasing to over 4000000 cP (milliPas) after a day's storage.

Example 8

In this Example, Example 3 was repeated, except that the same screw extruder was employed additionally as an in line compounder. A screw speed of 300 or 450 rpm was employed.

The composition within Formulation C above was compounded by feeding the constituents into the screw extruder in the following order:

The aqueous fluids were premixed and pumped at 70° C. via a metered pump into zone A, and the waxes were pre-melted and introduced via a metering pump into zone C at about 65 to 70° C. Zones A and B were maintained at approximately 80° C. to melt the waxes. The remaining minor ingredients, namely the pigment, and oils were introduced through a volume meter feeder in Zone J and the perfume was introduced via a gear pump in Zone K. The temperature of the segments after B was progressively lowered to a final segment temperature of about 40° C. This resulted in a fill temperature of about 42/43° C. The resultant product had an acceptable viscosity which had reached around 50000 cP (milliPas) within a day and over 150000 cP (milliPas) within a month.

This example shows that it is possible to manufacture an emulsion by an in-line compounding process.

Example 9

In this Example, Formulation G was made in a Betol twin screw extruder substantially according to FIG. 2, but having infeed at segments A, J and L, introducing a pre-formed mixture of carrier, structurant, perfume and rheology modifier into segment A after heating to a molten mass at about 70° C. via a heated dosing pump, a particulate antiperspirant active via a K-Tron into segment J attaining a temperature of about 65° C., and a moisturiser via a dosing pump at segment L at a temperature that was varied to provide a fill temperature in the range of from 52 to 67° C. The screw speed of the extruder was controlled in different runs at respectively 150, 250, 350 or 400 rpm.

| Formulation G | |
|---|---|
| Constituent | % by weight |
| Feed 1 | |
| cyclomethicone (DC245) | balance |
| Fatty acid triglyceride/ microcrystalline wax mixture 3:1 | 5.5–6.5 |
| Silicone elastomer/cyclomethicone (DC DC9040) | 18–22 |
| antioxidant | <0.2 |
| Perfume | 0.5–2% |
| Feed 2 | |
| AZAG tetrachlorhydrex glycine complex | 24–26 |
| Feed 3 | |
| Glycerol | 8–12 |

The product extruded from the extruder was filled into conventional 45 ml soft solid dispensers using a conventional cast fill apparatus.

The resultant products were assessed for sensory characteristics and appearance. The products obtained using a screw speed of over 300 rpm, viz 350 and 400 rpm and at a fill temperature of below 60° C. were assessed by the persons conducting the Example as having the best sensory properties, visually and to the touch being the smoothest, compared with products produced at a lower screw speed and a higher fill temperature.

The partial in-line compounding process of Example 9 for making a formulation comprising a suspension of a particulate antiperspirant in a structured hydrophobic phase was not only suitable for preparing a feedstock for a casting process, but likewise the feedstock is suitable for a subsequent injection moulding process.

What is claimed is:

1. A process for forming a deodorant or an antiperspirant soft solid product having a hardness of 0.003 to 0.5 Newtons/mm$^2$ which comprises a soft solid deodorant or antiperspirant composition stored in a dispensing container, the process comprising heating where necessary the deodorant or antiperspirant composition to form a mobile composition, delivering the mobile composition into a filling station and introducing over a period of time the mobile composition into the dispensing container wherein the mobile composition is injected into the dispensing container by an injector under a pressure of above 500 to 2000 kPa in an injection head of the injector for at least a fraction of the time in which the composition is being introduced into the dispensing container.

2. A process for forming a deodorant or an antiperspirant soft solid product according to claim 1 wherein the mobile composition is at least partially structured at the moment that it is injected into the dispensing container.

3. A process according to claim 1 wherein the deodorant or antiperspirant composition is at a temperature of not more than 5° C. above its regular set temperature when it enters the dispensing container.

4. A process according to claim 1 wherein the deodorant or antiperspirant composition is cooled whilst or before it is fed to the dispensing container.

5. A process according to claim 1 wherein the container is filled through the eventual top of the container.

6. A process according to claim 1 wherein the deodorant or antiperspirant soft solid is structured comprising a wax structurant or mixture of wax structurants.

7. A process according to claim 1 wherein the deodorant or antiperspirant soft solid is structured with an organic gellant.

8. A process according to claim 1 wherein the deodorant or antiperspirant soft solid comprises not more than 50% by weight particulate material, and preferably from 0 to 35% by weight.

9. A process according to any preceding claim characterised in that the deodorant or antiperspirant soft solid comprises up to 90% of a silicone oil.

10. A process for forming a deodorant or an antiperspirant soft solid product according to claim 1 wherein said soft solid composition has a viscosity of 10000 to 1000000 milliPas.

11. A process according to claim 1 wherein the deodorant or antiperspirant soft solid composition comprises up to 90% of a silicone oil.

12. A process according to a modification to claim 11 wherein the composition is an anhydrous solid.

13. A process according to claim 11 wherein the composition further comprises a polyhydric alcohol.

14. A process according to claim 13 wherein the polyhydric alcohol comprises glycerol.

15. A process according to claim 13 wherein the polyhydric alcohol is present in an amount of from 0.5 to 15% by weight.

16. A process according to claim 1 wherein individual constituents of the deodorant or antiperspirant composition are delivered to the filling station through a continuous mixer.

17. A process according to claim 16 wherein the mobile composition is produced by introducing the constituents of the composition into the mixer at a rate matched with the rate at which the composition is immediately filled by the filling station into the dispensing container.

18. A process according to claim 16 wherein the mixing is carried out in a screw extruder.

19. A process according to claim 18 wherein the screw extruder comprises two parallel screws with intermeshing flights.

20. A process according to claim 18 wherein the screw extruder is capable of heating the constituents to and maintain them in a mobile state.

21. A process according to claim 20 wherein the screw extruder comprises a plurality of segments, each of which is temperature controllable.

22. A process according to claim 21 wherein the temperatures of the segments in the screw extruder are controlled to provide a molten composition in the segment in which a meltable solid is introduced and the temperature falls progressively towards the segment from which the composition leaves the extruder.

23. A process according to claim 18 wherein individual constituents of the deodorant or antiperspirant composition are fed into the screw extruder at entry points spaced along the axis of the screw extruder.

24. A process according to claim 23 wherein a temperature sensitive constituent is introduced through the last entry point into the screw extruder.

25. A process according to claim 23 wherein the composition on leaving the extruder has a temperature that is higher than its structure impairment temperature and below its regular melting temperature.

26. A process according to claim 25 wherein the composition on leaving the extruder has a temperature of within 10° C. above or below its normal setting temperature.

27. A process according to claim 26 in which the composition on leaving the extruder has a temperature of within 5° C. of its normal setting temperature.

28. A process according to claim 1 or 2 wherein the deodorant or antiperspirant composition is injected employing an injection head pressure of 800 to 2000 kPa.

29. A process for producing a product comprising a deodorant or antiperspirant formulation in the form of a soft solid stored in a dispensing container comprising the steps of i) introducing individual constituents of said formulation into a twin screw extruder, ii) mixing said constituents to form a composition, iii) simultaneously with or subsequently to step ii) heating where necessary the constituents or the composition to render the composition mobile c and iv) transporting said mobile composition to an extruder outlet, wherein the formulation comprises a fluid carrier in which a particulate antiperspirant is suspended.

30. A process according to claim 29 wherein the screw extruder has two parallel screws with intermeshing flights.

31. A process according to claim 29 wherein the mobile composition discharged from the extruder outlet is filled into the dispensing container under pressure injection.

32. A process according to claim 29 wherein the mobile composition discharged from the extruder outlet is filled into the dispensing container by casting.

* * * * *